US007799758B2

(12) United States Patent
Petzelbauer et al.

(10) Patent No.: US 7,799,758 B2
(45) **Date of Patent: *Sep. 21, 2010**

(54) PEPTIDES AND PEPTIDE DERIVATIVES AS WELL AS PHARMACEUTICAL COMPOSITIONS CONTAINING THE SAME

(75) Inventors: Peter Petzelbauer, Vienna (AT); Rainer Henning, Uetliburg (CH); Sonja Reingruber, Vienna (AT)

(73) Assignee: Ikaria Development Subsidiary Two, LLC, Clinton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/678,535

(22) Filed: Feb. 23, 2007

(65) Prior Publication Data

US 2008/0039388 A1 Feb. 14, 2008

(30) Foreign Application Priority Data

Feb. 23, 2006 (AT) ............................... A 301/2006

(51) Int. Cl.
*A61K 38/16* (2006.01)
*C07K 14/00* (2006.01)

(52) U.S. Cl. .............................. 514/12; 514/2; 530/324

(58) Field of Classification Search ....................... None
See application file for complete search history.

(56) References Cited

U.S. PATENT DOCUMENTS

| | | | | |
|---|---|---|---|---|
| 4,966,848 | A * | 10/1990 | Smith et al. | 435/193 |
| 5,223,421 | A * | 6/1993 | Smith et al. | 435/193 |
| 5,837,218 | A * | 11/1998 | Peers et al. | 424/1.69 |
| 6,086,849 | A * | 7/2000 | Dean et al. | 424/1.69 |
| 6,323,311 | B1 * | 11/2001 | Liu et al. | 530/303 |
| 7,271,144 | B2 * | 9/2007 | Petzelbauer | 514/2 |
| 2004/0192596 | A1 * | 9/2004 | Petzelbauer | 514/12 |
| 2007/0037749 | A1 * | 2/2007 | Petzelbauer | 514/12 |
| 2008/0249006 | A1 * | 10/2008 | Petzelbauer et al. | 514/12 |
| 2009/0005310 | A1 * | 1/2009 | Petzelbauer et al. | 514/12 |

FOREIGN PATENT DOCUMENTS

| | | | |
|---|---|---|---|
| EP | 1 586 586 A2 | | 12/2001 |
| WO | 9216221 | | 10/1992 |
| WO | WO 92/16221 | * | 10/1992 |
| WO | 2004101600 | | 11/2004 |

OTHER PUBLICATIONS

Rudinger J, Peptide Hormones, Edited by J.A. Parsons, Characteristics of the amino acids as components of a peptide hormone sequence, 1976 print, pp. 1-7.*

Sigma Genosys, Designing Custom Peptides, pp. 1-2, Accessed on Dec. 16, 2004.*

Schinzel et al, The phosphate recognition site of *Escherichia coli* maltodextrin phosphorylase, FEBS, 1991, 286(1, 2): 125-128.*

Berendsen Herman J.C., A Glimpse of the Holy Grail?, Science, Oct. 23, 1998, 282: 642-643.*

Voet D and Voet JG, Biochemistry, Second Edition, John Wiley and Sons, Inc., 1995, pp. 235-241.*

Courtney MA, Bunce LA, Neroni LA, Simpson-Haidaris PJ, Cloning of the complete coding sequence of rat fibrinogen B-beta cDNA: interspecies conservation of fibrin beta15-42 primary structure, Blood Coagulation and Fibrinolysis, 1994, 5: 487-496.*

On-line Medical Dictionary—definition of derivative and analog, pp. 1-5. Accessed Jul. 7, 2005.*

Ngo JT, Marks J, Karplus M, "Computational complexity, protein structure prediction and the Levinthal Paradox," from The Protein Folding Problem and Tertiary Structure Prediction, K. Merc. Jr. and S. Le Grand, Editors, 1994, pp. 491-495.*

Bradley CM and Barrick D, "Limits of Cooperativity in a Structurally modular protein: Response of the Notch ANkyrin Domain to Analogous Alanine Substitutions in Each Repeat," Journal of Molecular Biology, 2002, 324: 373-386.*

U.S. Appl. No. 11/899,611, filed Sep. 6, 2007.*

U.S. Appl. No. 12/121,533, filed May 15, 2008.*

U.S. Appl. No. 12/121,544, filed May 15, 2008.*

U.S. Appl. No. 12/158,670, filed Sep. 15, 2008.*

U.S. Appl. No. 12/248,656, filed Oct. 9, 2008.*

U.S. Appl. No. 12/280,543, filed Sep. 30, 2008.*

Sang-Heon Lee, Seulki Lee, Yu Seok Youn, Dong Hee Na, Su Young Chae, Youngro Byun and Kang Choon Lee; Synthesis, Characterization, and Pharmacokinetic Studies of PEGylated Glucagon-like Paptide-1; Bioconjugate Chem.; Feb. 23, 2005; pp. 377-382.

R. J. M. Ross, K. C. Leung, M. Maamra, W. Bennett, N. Doyle, M. J. Waters and K. K. Y. Ho; Binding and Functional Studies with the Growth Hormone Receptor Antagonist, B2036-PEG (Pegvisomant), Reveal Effects of Pegylation and Evidence that it Binds to a Receptor Dimer; The Journal of Clinical Endocrinology & Metabolism; 2001; pp. 1716-1723; vol. 86, No. 4; USA.

Yasuo Tsutsumi, Tetsunari Kihira, Shin-Ichi Tsunoda, Naoki Okada, Yoshihisa Kaneda, Yoshiyuki Ohsugi, Masaharu Miyake, Shinsaku Nakagawa and Tadanori Mayumi; Polyethylene glycol modification of interleukin-6 enhances its thrombopoietic activity; ScienceDirect—Journal of Controlled Release; Mar. 1995; pp. 447-451; vol. 33, Issue 3, Abstract Only.

(Continued)

*Primary Examiner*—Julie Ha
(74) *Attorney, Agent, or Firm*—Hoffmann & Baron, LLP

(57) ABSTRACT

Therapeutic compositions can include modified peptides which are derived from the chain of the Bbeta(15-42)-fibrin fragment and wherein one or several of the amino acids of the sequence have been substituted by genetically encoded or not genetically encoded amino acids or peptidomimetics. They may exist as free peptides or as C-terminal derivative and/or being linked to a polyethylene glycol (PEG)-polymer, and have anti-inflammatory and/or endothelium stabilizing effects. Esters or amides may for instance be taken into consideration as C-terminal derivatives. Processes for production of the peptides and derivatives thereof are also described.

4 Claims, 1 Drawing Sheet

OTHER PUBLICATIONS

Paolo Caliceti and Francesco M. Veronese; Pharmacokinetic and biodistribution properties of poly(ethylene glycol)-protein conjugates; ScienceDirect—Advanced Drug Delivery Reviews; Sep. 26, 2003; pp. 1261-1277; vol. 55, Issue 10, Abstract Only.

Michael J. Knauf, Dick P. Bell, Pam Hirtzer, Zhen-Ping Luo, John D. Young and Nandini V. Katre; Relationship of Effective Molecular Size to Systemic Clearance in Rats of Recombinant Interleukin-2 Chemically Modified with Water-soluble Polymers; The Journal of Biological Chemistry; Oct. 15, 1988; pp. 15064-15070; vol. 263, Issue of Oct. 15; USA.

P. Esposito, L. Barbero, P. Caccia, P. Caliceti, M. D'Antonio, G. Piquet and F. M. Veronese; PEGylation of growth hormone-releasing hormone (GRF) analogues; ScienceDirect—Advanced Drug Delivery Reviews; Sep. 26, 2003; pp. 1279-1291; vol. 55, Issue 10, Abstract Only.

Kang Choon Lee, Seung Cheol Moon, Myung Ok Park, Jung Tae Lee, Dong Hee Na, Sun Dong Yoo, Hye Suk Lee, and Patrick P. DeLuca; Isolation, Characterization, and Stability of Positional Isomers of Mono-PEGylated Salmon Calcitonins; Pharmaceutical Research; Jun. 1999; pp. 813-818; vol. 16, No. 6/Jun. 1999; Netherlands, Abstract Only.

Abraham Abuchowski, John R. McCoy, Nicholas C. Palczuk, Theo Van ES and Frank F. Davis; Effect of Covalent Attachment of Polyethylene Glycol on Immunogenicity and Circulating Life of Bovine Liver Catalase; The Journal of Biological Chemistry; Jun. 10, 1977; pp. 3582-3586; vol. 252, No. 11; USA.

Kita Y, Rohde MF, Arakawa T, Fagin KD, Fish EN, Banerjee K; Characterization of a polyethylene glycol conjugate of recombinant human interferon-gamma; Drug Des Deliv.; Sep. 1990; 6(3):157-67, Abstract Only.

Harris JM, Chess RB; Effect of pegylation on pharmaceuticals; Nat Rev Drug Discov.; Mar. 2003; 2(3):214-21; USA, Abstract Only.

* cited by examiner

PEPTIDES AND PEPTIDE DERIVATIVES AS WELL AS PHARMACEUTICAL COMPOSITIONS CONTAINING THE SAME

The present invention relates to peptides and peptide derivatives, to the production thereof as well as to their use for preparing a therapeutically and/or preventively active drug and to such a pharmaceutical drug.

EP1586586 describes the use of peptides from the sequence of fibrin possessing anti-inflammatory effects.

Said effect may be based on the fact that the fibrin and fibrin fragments generated during the breakdown thereof bind to endothelial cells via its neo-N-terminus of the Bbeta-chain and to cells in the bloodstream via the sequence of the Aalpha-chain, thereby leading to the adhesion and transmigration of these cells into the tissue. The binding partner of the fibrin and fibrin fragments to the endothelial cells is the protein vascular endothelial (VE) cadherin, which is expressed exclusively in the adherens junction between neighboring endothelial cells. The peptides according to the invention block this interaction and thereby counteract the transmigration of blood cells. The natural defense against infections by the leukocytes in the blood is not adversely effected, however. Thus, the composition of the same, such as granulocytes, lymphocytes and monocytes, remains unaffected so that the natural defense process is maintained.

Fibrinogen is produced in the liver and, in this form, is biologically inactive and normally is provided in the blood at concentrations of around 3 g/l. Proteolytic cleavage of the proenzyme prothrombin results in the formation of thrombin, which cleaves off the fibrinopeptides A and B from the fibrinogen. In this way, fibrinogen is transformed into its biologically active form. Fibrin and fibrin cleavage products are generated.

Thrombin is formed whenever blood coagulation is activated, i.e. with damage to the tissue, be it of inflammatory, traumatic or degenerative genesis. The formation of fibrin as mediated by thrombin is basically a protective process aimed at quickly sealing any defects caused to the vascular system. However, the formation of fibrin also is a pathogenic process. The appearance of a fibrin thrombus as the triggering cause of cardiac infarction is one of the most prominent problems in human medicine.

The role which fibrin plays during the extravasation of inflammatory cells from the bloodstream into the tissue, which, on the one hand, is a desired process for the defense against pathogenic microorganisms or tumor cells in the tissue, but, on the other hand, is a process which, by itself, induces or prolongs damage done to the tissue, has so far not been examined at all or not to a sufficient extent. Fibrin binds to endothelial cells via its neo-N-terminus of Bbeta by means of the sequence to Bbeta and to cells in the bloodstream by means of the sequence Aalpha, thereby leading to the adhesion and transmigration of cells into the tissue.

By way of the mechanism described above the peptides or proteins according to the invention may prevent the adhesion of cells from the bloodstream to endothelial cells of the vascular wall and/or their subsequent transmigration from the blood into the tissue.

WO9216221 describes polypeptides which are covalently linked to long-chain polymers, as for instance methoxy-polyethylene glycol (PEG). The binding of polypeptides to such polymers frequently results in a prolongation of the biological half-life of these polypeptides and delays their renal excretion. A summary of these properties may be found in Davis et al., Polymeric Materials Pharmaceuticals for Biomedical Use, pp. 441-451 (1980) The addition of PEG-groups exerts this effect in a way proportional to the molecular weight of the PEGylated peptide, as, up to a certain size of the molecule, the glomular filtration rate is inversely proportional to the molecular weight.

WO2004/101600 also describes new poly(ethylene glycol)-modified compounds and their use, in particular with emphasis on modified peptides activating the erythropoietin receptor.

Further examples for the covalent modification of peptides and proteins PEG residues are interleukins (Knauf et al., J. Biol. Chem. 1988, 263, 15064; Tsutumi et al., J. Controlled Release 1995, 33, 447), Interferons (Kita et al., Drug Delivery Res. 1990, 6 157), Catalase (Abuchowski et al., J. Biol. Chem. 1997, 252, 3582). A review of the prior art may be found in Reddy, Ann. of Pharmacotherapy, 2000, 34, 915.

A prolonged biological half-life is advantageous for various therapeutic uses of peptides. This is in particular true in cases of chronic diseases where the administration of the active agent over a prolonged period of time is indicated. With such indications this may improve the patient's compliance, as applying the active agent once a day will for instance be accepted more easily than continuous infusion. Apart from increasing the molecular mass by covalent modification, a prolongation of the persistency of polypeptides may be obtained by modifying them in such a way that their degradation by proteolytic enzymes (e.g. exo- or endoproteases or peptidases) is prevented.

Using various examples it has been shown that it is necessary to customize the appropriate modification for each peptide so as to prevent a significant influence on the pharmacodynamic effect as compared to the unmodified peptide. In this context the following may be referred to: Calcitonin (Lee et al. Pharm. Res. 1999, 16, 813), Growth Hormone Releasing Hormone (Esposito et al., Advanced Drug Delivery Reviews, 2003, 55, 1279), Glucagon like peptide 1 (Lee et al., Bioconjugate Res. 2005, 16, 377), as well as the growth hormone-receptor antagonist Pegvisomant (Ross et al., J. Clin. Endocrin. Metab. 2001, 86, 1716). The reviews by Caliceti and Veronese (Adv. Drug Deliv. Rev. 2003, 55 1261) and by Harris and Chess (Nature Rev. Drug Discovery 2003, 2, 214) discuss that in case of designing peptide- or protein-PEG-conjugates it is necessary to take into consideration the structure of the original substance, the molecular weight of the peptide and the polymer, the number of conjugated polymer chains as well as the linker chemistry, so as to obtain an effective peptide-PEG-conjugate.

Surprisingly it has now been found that peptides derived from the chain of the Bbeta(15-42) fibrin fragment, wherein one or several amino acids of the natural fibrin sequence have been substituted by other amino acids, as well as derivatives modified at the C-terminal end of the peptide sequence also have strong anti-inflammatory effects. The same applies to peptides and peptide derivatives the modification of which prevents their destruction by proteases or peptidases, as well as to peptide-PEG-conjugates derived from the basic sequence of the Bbeta(15-42) fibrin fragment.

Thus the invention relates to modified peptides which are derived from the chain of the Bbeta(15-42)-fibrin fragment and wherein one or several of the amino acids of the sequence have been substituted by genetically encoded or not genetically encoded amino acids or peptidomimetics. They may exist as free peptides or as C-terminal derivative and/or being linked to a polyethylene glycol (PEG)-polymer, and have anti-inflammatory and/or endothelium stabilizing effects. Esters or amides may for instance be taken into consideration as C-terminal derivatives.

The inventive compounds may have conservative substitutions of amino acids as compared to the natural sequence of fibrin of the warm blooded animals to be treated in one or several positions. A conservative substitution is defined as the side chain of the respective amino acid being replaced by a side chain of similar chemical structure and polarity, the side chain being derived from a genetically coded or not genetically coded amino acid. Families of amino acids of this kind having similar side chains are known in the art. They comprise for instance amino acids having basic side chains (lysins, arginins, histidine), acidic side chains (aspartic acid, glutamic acid), uncharged polar side chains (glycine, aspartamic acid, glutamine, serine, threonine, tyrosine, cysteine), non-polar side chains (alanine, valine, leucine, isoleucine, proline, phenylalanine, methionine, tryptophan), beta-branched side chains (threonine, valine, isoleucine) and aromatic side chains (tyrosine, phenylalanine, tryptophane, histidine). Such conservative substitutions of side chains may preferably be carried out in non-essential positions. In this context, an essential position in the sequence is one wherein the side chain of the relevant amino acid is of significance for its biological effect.

The invention in particular concerns peptides and peptide derivatives of the following general formula I:

$$H_2N\text{-}GHRPX_1X_2X_3X_4X_5X_6X_7X_8PX_9X_{10}X_{11}P\,X_{12}PPPX_{13}X_{14}X_{15}X_{16}GYR\text{-}X_{17} \quad (I),$$

wherein:

$X_1$-$X_{16}$ denote one of the 20 genetically encoded amino acids, $X_{17}$ denotes $OR_1$ with $R_1$=hydrogen or ($C_1$-$C_{10}$)-alkyl, or $NR_2R_3$, $R_2$ and $R_3$ being identical or different and denoting hydrogen, ($C_1$-$C_{10}$)-alkyl, or a residue -$PEG_{5\text{-}60K}$, wherein the PEG-residue is linked to the N atom via a spacer (SEQ ID NO: 1), or a residue NH-Y-Z-$PEG_{5\text{-}60K}$, wherein Y denotes a chemical bond or a genetically coded amino acid from among the group of S, C, K or R, and Z denotes a spacer by way of which a polyethylene glycol (PEG)-residue may be linked (SEQ ID NO: 2), as well as the physiologically acceptable salts thereof, or wherein $X_{15}$ or $X_{16}$ denote an amino acid from the group of C or K, which is linked to a residue Z-$PEG_{5\text{-}60K}$ via the heteroatom in the side chain, and wherein $X_{17}$ denotes $OR_1$, with $R_1$=hydrogen or ($C_1$-$C_{10}$)-alkyl, or $NR_2R_3$, $R_2$ and $R_3$ being identical or different and denoting hydrogen or ($C_1$-$C_{10}$)-alkyl (SEQ ID NO: 3), as well as the physiologically acceptable salts thereof.

A preferred subject matter of the invention are peptides and peptide derivatives of the general Formula I, wherein:

$X_1$, $X_9$, $X_{10}$, $X_{14}$ denote L, I, S, M or A, $X_2$, $X_6$, $X_7$ denote E or D, $X_3$, $X_4$, $X_5$, $X_{11}$ denote R or K $X_8$, $X_{12}$ denote A, G, S, or L $X_{13}$ denotes I, L or V and wherein $X_{15}$, $X_{16}$ and $X_{17}$ have the same meaning as given above, namely, $X_{15}$-$X_{16}$ denote one of the 20 genetically encoded amino acids, $X_{17}$ denotes $OR_1$ with $R_1$=hydrogen or ($C_1$-$C_{10}$)-alkyl, or $NR_2R_3$, $R_2$ and $R_3$ being identical or different and denoting hydrogen, ($C_1$-$C_{10}$)-alkyl, or a residue -$PEG_{5\text{-}60}$, wherein the PEG-residue is linked to the N atom via a spacer (SEQ ID NO: 4), or a residue NH-Y-Z-$PEG_{5\text{-}60K}$, wherein Y denotes a chemical bond or a genetically coded amino acid from among the group of S, C, K or R, and Z denotes a spacer by way of which a polyethylene glycol (PEG)-residue may be linked (SEQ ID NO: 5), as well as the physiologically acceptable salts thereof, or wherein $X_{15}$ or $X_{16}$ denote an amino acid from the group of C or K, which is linked to a residue Z-$PEG_{5\text{-}60K}$ via the heteroatom in the side chain, and wherein $X_{17}$ denotes $OR_1$, with $R_1$=hydrogen or ($C_1$-$C_{10}$)-alkyl, or $NR_2$, $R_3$, $R_2$ and $R_3$ being identical or different and denoting hydrogen or ($C_1$-$C_{10}$)-alkyl (SEQ ID NO: 6), as well as the physiologically acceptable salts thereof.

A particularly preferred subject matter of the invention are peptides and peptide derivates of Formula II, $$H_2N\text{-}GHRPLDKKREEAPSLRPAPPPISGGGYR\text{-}X_{17} \quad (II),$$

wherein $X_{17}$ has the same meaning as given above for Formula I, namely, $X_{17}$ denotes $OR_1$ with $R_1$=hydrogen or ($C_1$-$C_{10}$)-alkyl, or $NR_2R_3$, $R_2$ and $R_3$ being identical or different and denoting hydrogen, ($C_1$-$C_{10}$)-alkyl, or a residue -$PEG_{5\text{-}60K}$, wherein the PEG-residue is linked to the N atom via a spacer (SEQ ID NO: 7), or a residue NH-Y-Z-$PEG_{5\text{-}60K}$, wherein Y denotes a chemical bond or a genetically coded amino acid from among the group of S, C, K or R, and Z denotes a spacer by way of which a polyethylene glycol (PEG)-residue may be linked (SEQ ID NO: 8), as well as the physiologically acceptable salts thereof.

A most highly preferred subject matter of the present invention are compounds of Formula (II), wherein $X_{17}$ denotes $NR_2R_3$, $R_2$ and $R_3$ being identical or different and being hydrogen or ($C_1$-$C_{10}$)-alkyl, or a residue C($NR_2R_3$)-(S-succinimido)-($PEG_{5\text{-}40K}$), the succinimide residue being linked via C-atom 3 to the sulfur atom of the cysteine residue (SEQ ID NO: 9) as well as the physiologically acceptable salts thereof.

A furthermore most highly preferred subject matter of the invention are peptide derivatives of Formula (III), $$H_2N\text{-}GHRPLDKKREEAPSLRPAPPPIS\text{-}X_{19}\text{-}X_{20}\text{-}X_{21}\text{-}YR\text{-}X_{17} \quad (III)$$

wherein two of the residues $X_{19}$, $X_{20}$ and $X_{21}$ each are a glycine residue and the remaining one is a residue C-(S-succinimido)-($PEG_{5\text{-}40K}$), the succinimido residue being linked to the sulfur atom of the cysteine residue via C-atom 3, and wherein $X_{17}$ denotes $NR_2R_3$, $R_2$ and $R_3$ being identical or different and being hydrogen or ($C_1$-$C_{10}$)-alkyl (SEQ ID NO: 10), as well as the physiologically acceptable salts thereof.

A furthermore most highly preferred subject matter of the invention are peptide derivatives of Formula (III), $$H_2N\text{-}GHRPLDKKREEAPSLRPAPPPIS\text{-}X_{19}\text{-}X_{20}\text{-}X_{21}\text{-}YR\text{-}X_{17} \quad (III)$$

wherein two of the residues $X_{19}$, $X_{20}$ and $X_{21}$ each are a glycine residue and the remaining one is a residue K-($PEG_{5\text{-}40K}$), the PEG-residue being linked via the nitrogen atom in the side chain of the lysine residue, and wherein $X_{17}$ denotes $NR_2R_3$, $R_2$ and $R_3$ being identical or different and being hydrogen or ($C_1$-$C_{10}$)-alkyl (SEQ ID NO: 11), as well as the physiologically acceptable salts thereof.

In the above formulas I and II the following letters represent amino acid residues in accordance with the general annotation for proteins and peptides: pPhenylalanine is F, leucine is L, isoleucine is I, methionine is M, valine is V, serine is S, proline is P, threonine is T, alanine is A, tyrosine is Y, histidine is H, glutamine is Q, asparagine is N, lysine is K, aspartic acid is D, glutamic acid is E, cysteine is C, tryptophan is W, arginine is R, glycine is G.

The amino acid residues in the compounds of Formula I may either be present in their D or their L configuration.

The term peptide refers to a polymer of these amino acids, which are linked via an amide linkage.

Figure 1:
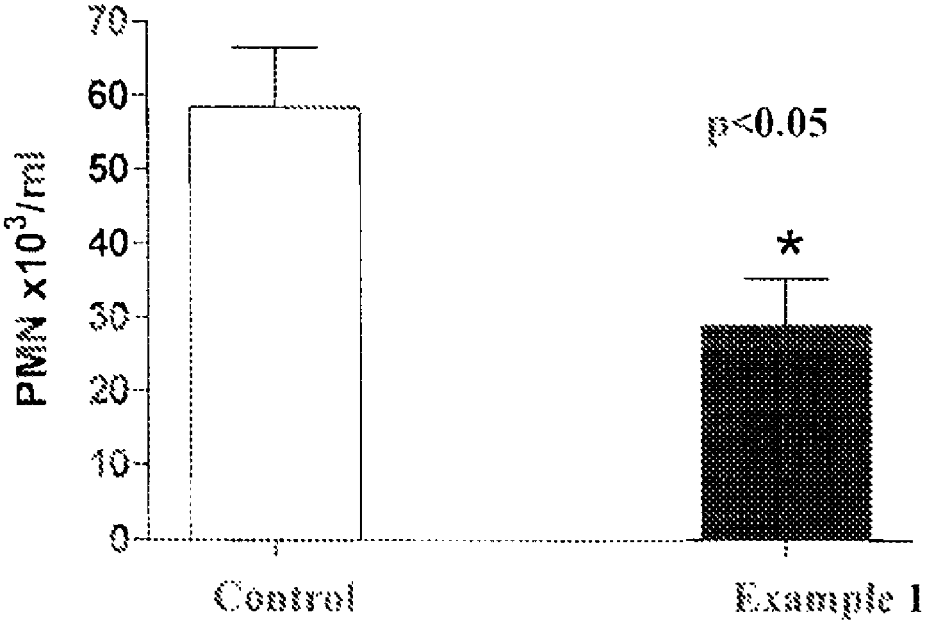
FIG. 1 is a bar graph illustrating the number of neutrophils, specifically polymorphonuclear leukocytes (PMN), present in bronchioalvelolar lavage liquid of mice having LPS-induced pneumonitis treated with either Control (100 μl NaCl) or 4.8 mg/kg of the agent of Example 1 (dissolved in 100 μl NaCl).

"Physiologically acceptable" means that salts are formed with acids or bases the addition of which does not have undesirable effects when used for humans. Preferable are salts with acids or bases the use of which is listed for use with warm blooded animals, in particular humans, in the US Pharmacopoeia or any other generally recognized pharmacopoeia.

PEG stands for a polyethylene glycol residue having a molecular weight of between 5.000 and 60.000 Dalton, this molecular weight being the maximum of a molecular weight distribution, so that individual components of the mixture may have a higher or lower molecular weight.

The invention furthermore concerns processes for the production of the peptides and peptide derivatives of general Formula (I), characterized in that, either (A) the first amino acid at the C-terminal end of the respective sequence is linked to a polymeric resin via a suitable cleavable spacer, the subsequent amino acids, optionally containing suitable protective groups for functional groups, are linked step by step according to methods known in the art, the finished peptide is cleaved off the polymeric resin according to suitable methods known in the art, the protective groups, if present, are cleaved off by suitable methods and the peptide or peptide derivative is purified according to suitable methods, or (B) a PEG-group having a desired molecular weight is linked to a polymeric resin via a suitable spacer, the first amino acid at the N-terminal end of the peptide is linked using suitable methods, the remaining steps being the same as described in (A), or (C) a lysine residue, containing a suitable protective group at the ε-amino group is linked to a suitable polymeric resin via a suitable spacer using suitable methods, the peptide chain is synthesized as described in (A), following cleavage from the polymeric resin and purification, if necessary, the protective group at the ε-amino group is cleaved off using suitable methods, a PEG group having a desired molecular weight is linked to the ε-amino group using a suitable activated reagent, the optionally remaining protective groups are cleaved off and the final product is purified using suitable methods, or (D) a peptide containing a cysteine residue is reacted with a PEG-maleimide to form compounds of Formula (III).

Suitable processing steps following (A), (B) or (C) as well as suitable reagents are for instance described in document WO 2004/101600.

Embodiments of the respective processing steps are not new per se and will be clear to an experienced specialist in the field of organic synthesis.

Processes for linking a PEG-residue to a peptide chain will be known to the skilled artisan. For instance, a cysteine (C)-residue may be reacted with PEG-maleimide, resulting in a succinimide residue as spacer for residue Z. A further possibility is reacting an optionally activated C-terminal carboxy residue with an aminoalkyl-substituted PEG residue. A further possibility is the introduction of a PEG residue by reacting an aldehyde-substituted PEG residue with the ε-amino function of a lysine residue. Activated PEG reagents having suitable spacers and reactive groups may for instance be obtained from NOF Corporation (Tokyo, Japan).

The substances according to the invention and the use of the substances according to the invention for the production of a pharmaceutical drug are of particular significance for the production of a pharmaceutical drug for the therapy of diseases resulting from the tissue-damaging effect of white blood cells, or wherein the integrity and full physiological integrity of the layer of endothelial cells lining the blood vessels is impaired.

Diseases belonging to this group are those in context with autoimmunity, as for instance collagenoses, rheumatic diseases, inflammatory bowel diseases like Morbus Crohn or Colitis ulcerosa, psoriasis and psoriatic rheumatoid arthritis, and post/parainfectious diseases as well as diseases caused by a graft-versus-host reaction. A healing effect takes place as this medical drug blocks the migration of the white blood cells into the tissue. Thus the white blood cells remain in the blood stream and cannot cause an autoreactive effect harmful to the tissue. This effect of the inventive substances is furthermore important for the treatment of shock conditions, in particular in case of septic shock triggered by infection with gram-positive or gram-negative bacterial pathogens as well as viral infections and haemorrhagic shock caused by heavy loss of blood because of severe injuries or bacterial or viral infections.

The inventive substances may generally be used in situations that can be described with the terms "Systemic Inflammatory Response Syndrome (SIRS)", "Acute Respiratory Distress Syndrome (ARDS)" and organ- or multiorgan failure, respectively.

With a pharmaceutical drug for the therapy and/or prevention of rejection reactions of organ transplants there is a healing effect as this pharmaceutical drug prevents the migration of white blood cells from the blood stream into the donor organ, and the donor organ can therefore not be destroyed for instance by autoreactive lymphocytes.

With a pharmaceutical drug for the therapy and/or prevention of arteriosclerosis there is a healing and/or preventive effect as this pharmaceutical drug blocks the migration of lymphocytes and monocytes into the wall of the tissue and thus the activation of the cells of the tissue wall. Thus the progress of arteriosclerosis is minimized or stopped, the progredience of arteriosclerotic plaque resulting therefrom is inhibited, causing the arteriosclerosis to recede.

With a pharmaceutical drug for the therapy and/or prevention of reperfusion trauma following surgically or pharmaceutically induced re-supply with blood, e.g. following percutaneous coronary intervention, stroke, vessel surgery, cardiac bypass surgery and organ transplants, there is a healing and/or preventive effect as this pharmaceutical drug inhibits the migration of lymphocytes, neutrophils and monocytes into the wall of the vessel. Reperfusion trauma is caused by a lack of oxygen/acidosis of the cells of the vessel during its re-supply with blood, leading to their activation and/or damage. Because of this, lymphocytes, neutrophils and monocytes adhere to the vessel wall and migrate into it. Blocking the adherence and migration of lymphocytes, neutrophils and monocytes in the vessel wall causes the hypoxy/acidosis-induced damage to abate, without the subsequent inflammatory reaction causing a permanent damage to the vessel. The endothelium-stabilizing effect of the inventive compounds furthermore prevents the formation of oedemas as well as any further damage to the organs supplied via the respective blood vessels.

With a pharmaceutical drug for the therapy and/or prevention of arteriosclerosis as a consequence of metabolic diseases or the process of aging, there is a healing and/or preventive effect as this pharmaceutical drug inhibits the migration of lymphocytes, neutrophils and monocytes into the vessel wall, thus inhibiting the progredience of arteriosclerotic plaque resulting thereform.

The pharmaceutical drug according to the invention may also be used for the transportation of another drug. The inventive drug specifically binds a surface molecule on endothelial cells. Thus drugs linked thereto may be delivered to endothelial cells in high concentrations without any danger of them having side effects at other sites. An example that may be cited here is the use of substances inhibiting the division of cells, which, specifically brought to endothelial cells, may have an antiangiogenetic effect. This brings about a healing effect in tumor patients, as tumor growth is blocked by preventing the proliferation of endothelial cells and thus by preventing neoangiogenesis. The inventive compounds themselves may also develop an antiangiogenetic effect, as they, because of their endothelium-stabilizing effect, prevent the endothelial cells from changing into a proliferative phenotype and thus prevent the formation of new capillary blood vessels. Therefore they are themselves suitable for the treatment of all kinds of tumor diseases as well as the prevention and/or treatment of tumor metastases.

The inventive compounds of Formula (I) together with pharmaceutical adjuvants and additives, may be formulated into pharmaceutical preparations which also are a subject matter of the present invention. In order to prepare such formulations a therapeutically effective dose of the peptide or peptide derivative is mixed with pharmaceutically acceptable diluents, stabilizers, solubilizers, emulsifying aids, adjuvants or carriers and brought into a suitable therapeutic form. Such preparations for instance contain a dilution of various buffers (e.g. Tris-HCl, acetate, phosphate) of different pH and ionic strength, detergents and solubilizers (e.g. Tween 80, Polysorbat 80), antioxidants (e.g. ascorbic acid), and fillers (e.g. lactose, mannitol). These formulations may influence the biological availability and the metabolic behavior of the active agents.

The pharmaceutical preparations according to the invention may be administered orally, parenterally (intramuscularly, intraperitoneally, intravenously or subcutaneously), transdermally or in an erodable implant of a suitable biologically degradable polymer (e.g. polylactate or polyglycolate).

The biological effect and applicability for the claimed use of the inventive compounds may for instance be determined in an assay in which a culture of human umbilical cord endothelial cells is examined microscopically after stimulation with the "N-terminal disulfide knot protein II" (NDSK-II) or with thrombin. The stimulation of endothelial cells causes the formation of gaps between the cells in a densely packed cell layer. Treatment with the inventive compounds may prevent the formation of these gaps, and is successful in closing gaps that have already been formed. This effect is predicative for the protective effect on the endothelium the inventive compounds have throughout the organism. The inventive compounds have an effect in the range of concentrations from 0.01 nM to 1 mM, preferably in the range from 1 nM to 0.1 mM in the bath solution of cells.

The effectiveness in vivo may for instance be established using a model of acute pulmonitis in a rodent. For this the treatment of the animal and the administration of the substance are carried out as described in Example 7 below. The inventive compounds show an effect at a dose ranging from 0.001 mg/kg body weight to 500 mg/kg body weight, preferably at a dose ranging from 0.1 mg/kg to 50 mg/kg.

A further possibility for establishing the biological effect in vivo is the reduction or complete suppression of mortality because of an infection with haemolytic viruses or bacteria. For this purpose, mice are, as described in Example 8, for instance infected with a dose of Dengue viruses, wherein 50% of the animals die within a period of 5-20 days after infection. The inventive compounds bring about a reduction of this mortality at a dose ranging from 0.001 to 500 mg/kg body weight, preferably at a dose ranging from 0.1 to 50 mg/g body weight.

The following examples serve to illustrate the invention without limiting it to the examples.

General Preparation and Purification of Peptides According to the Invention

The preparation and purification of the above peptide derivatives generally takes place by way of FMOC-strategy on acid-labile resin supports using a commercially available batch peptide synthesizer as also described in the literature (e.g. "solid phase peptide synthesis—A practical approach" by E. Atherton, R. C. Sheppard, Oxford University press 1989). N-alpha-FMOC-protected derivatives, the functional side-chains of which are protected by acid-sensitive protective groups, are used as amino acid components. Unless otherwise stated, purification is carried out by means of RP-chromatography using a water/acetonitrile gradient and 0.1% TFA as ion pair reagent.

EXAMPLE 1

(SEQ ID NO: 12)
Gly-His-Arg-Pro-Leu-Asp-Lys-Lys-Arg-Glu-Glu-Ala-
Pro-Ser-Leu-Arg-Pro-Ala-Pro-Pro-Pro-Ile-Ser-Gly-
Gly-Gly-Tyr-Arg-NH$_2$ 100 mg Tentagel-S-RAM (Rapp-Polymere) at a load of 0.24 mmol/g are transferred to a commercially available peptide synthesis device (PSMM(Shimadzu)), wherein the peptide sequence is constructed step-by-step according to the carbodiimide/HOBt method.

The FMOC-amino acid derivatives are pre-activated by adding a 5-fold equimolar excess of di-isopropy-carbodiimide (DIC), di-isopropy-ethylamine (DIPEA) und hydroxybenzotriazole (HOBt) and, following their transfer into the reaction vessel, mixed with the resin support for 30 minutes. Washing steps are carried out by 5 additions of 900 μl DMF and thorough mixing for 1 minute. Cleavage steps are carried out by the addition of 3×900 μl 30% piperidine in DMF and thorough mixing for 4 minutes.

Removal of the individual reaction and wash solutions is effected by forcing the solutions through the bottom frit of the reaction vessel.

The amino acid derivatives FMOC-Ala, FMOC-Arg(Pbf), FMOC-Asp, FMOC-Gly, FMOC-His(Trt), FMOC-Ile, FMOC-Leu, FMOC-Lys(BOC), FMOC-Pro, FMOC-Ser (tBu) and FMOC-Tyr(tBu) (Orpegen) are employed.

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 μm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained Maldi-TOF, 3036.6 m/z (m.i.).

EXAMPLE 2

(SEQ ID NO: 13)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-succinimido-$PEG_{20K}$)-OH The monomeric peptide is synthesized as in Example 1, Tentagel (Rapp Polymere) being used as resin support here with FMOC-Cys(Trt) as the first amino acid.

After cleavage and purification of the peptide reaction is carried out with a 2- to 8-fold molar excess of maleinimido-$PEG_{20}$ K. Following recovery purification is carried out on Kromasil RP-18, and the identity of the product is confirmed by way of analytical RP-HPLC and MALDI-MS.

EXAMPLE 3

(SEQ ID NO: 14)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-succinimido-$PEG_{20K}$)-amide 100 mg Tentagel-S-RAM (Rapp-Polymere) at a load of 0.24 mmol/g are transferred to a commercially available peptide synthesis device (PSMM(Shimadzu)), wherein the peptide sequence is constructed step-by-step according to the carbodiimide/HOBt method.

The FMOC-amino acid derivatives are pre-activated by adding a 5-fold equimolar excess of di-isopropy-carbodiimide (DIC), di-isopropy-ethylamine (DIPEA) und hydroxybenzotriazole (HOBt) and, following their transfer into the reaction vessel, mixed with the resin support for 30 minutes. Washing steps are carried out by 5 additions of 900 μl DMF and thorough mixing for 1 minute. Cleavage steps are carried out by the addition of 3×900 μl 30% piperidine in DMF and thorough mixing for 4 minutes.

Removal of the individual reaction and wash solutions is effected by forcing the solutions through the bottom frit of the reaction vessel.

The amino acid derivatives FMOC-Ala, FMOC-Arg(Pbf), FMOC-Asp, FMOC-Gly, FMOC-His(Trt), FMOC-Ile, FMOC-Leu, FMOC-Lys(BOC), FMOC-Pro, FMOC-Ser (tBu), FMOC-Cys(Trt) and FMOC-Tyr(tBu) (Orpegen) are employed.

After cleavage and purification of the peptide reaction is carried out with a 2- to 8-fold molar excess of maleinimido-$PEG_{20}$ K. Following recovery purification is carried out on Kromasil RP-18, and the identity of the product is confirmed by way of analytical RP-HPLC and MALDI-MS.

EXAMPLE 4

(SEQ ID NO: 15)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Cys-(S-succinimido-$PEG_{20K}$)-Gly-Tyr-Arg-amide 100 mg Tentagel-S-RAM (Rapp-Polymere) having a charge of 0.24 mmol/g are transferred to a commercially available peptide synthesis device (PSMM(Shimadzu)), wherein the peptide sequence is constructed step-by-step according to the carbodiimide/HOBt method.

The FMOC-amino acid derivatives are pre-activated by adding a 5-fold equimolar excess of di-isopropy-carbodiimide (DIC), di-isopropy-ethylamine (DIPEA) und hydroxybenzotriazole (HOBt) and, following their transfer into the reaction vessel, mixed with the resin support for 30 minutes. Washing steps are carried out by 5 additions of 900 μl DMF and thorough mixing for 1 minute. Cleavage steps are carried out by the addition of 3×900 μl 30% piperidine in DMF and thorough mixing for 4 minutes.

Removal of the individual reaction and wash solutions is effected by forcing the solutions through the bottom frit of the reaction vessel.

The amino acid derivatives FMOC-Ala, FMOC-Arg(Pbf), FMOC-Asp, FMOC-Gly, FMOC-His(Trt), FMOC-Ile, FMOC-Leu, FMOC-Lys(BOC), FMOC-Pro, FMOC-Ser (tBu), FMOC-Cys(Trt) and FMOC-Tyr(tBu) (Orpegen) are employed.

When synthesis is completed the peptide resin is dried. The peptide amide is subsequently cleaved by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20. The peptide thus obtained is reacted with maleinimido-$PEG_{20}$ k. Following recovery, purification by means of gel chromatography and lyophilisation a pure product is obtained, the identity of which is confirmed by way of RP-HPLC and MALDI-MS.

EXAMPLE 5

(SEQ ID NO: 16)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Cys-(S-succinimido-$PEG_{20K}$)-Gly-Gly-Tyr-Arg-amide It is obtained as in Example 4, the sequence of protected amino acids being appropriately altered.

EXAMPLE 6

(SEQ ID NO: 17)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Cys-(S-succinimido-$PEG_{20K}$)-Tyr-Arg-amide It is obtained as in Example 4, the sequence of protected amino acids being appropriately altered.

The following were prepared as in Example 1

(SEQ ID NO: 18)
Gly-His-Arg-Pro-Ile-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-$NH_2$ (SEQ ID NO: 19)
Gly-His-Arg-Pro-Ala-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-$NH_2$ (SEQ ID NO: 20)
Gly-His-Arg-Pro-Leu-Asp-Arg-Lys-Arg-Glu-Glu-Ala-Pro-Ser-Leu-Arg-Pro-Ala-Pro-Pro-Pro-Ile-Ser-Gly-Gly-Gly-Tyr-Arg-$NH_2$ (SEQ ID NO: 21)
Gly-His-Arg-Pro-Leu-Asp-Lys-Arg-Arg-Glu-Glu-Ala-Pro-Ser-Leu-Arg-Pro-Ala-Pro-Pro-Pro-Ile-Ser-Gly-Gly-Gly-Tyr-Arg-$NH_2$ (SEQ ID NO: 22)
Gly-His-Arg-Pro-Leu-Asp-Lys-Lys-Arg-Asp-Glu-Ala-Pro-Ser-Leu-Arg-Pro-Ala-Pro-Pro-Pro-Ile-Ser-Gly-Gly-Gly-Tyr-Arg-$NH_2$ (SEQ ID NO: 23)
Gly-His-Arg-Pro-Leu-Asp-Lys-Lys-Arg-Glu-Asp-Ala-Pro-Ser-Leu-Arg-Pro-Ala-Pro-Pro-Pro-Ile-Ser-Gly-Gly-Gly-Tyr-Arg-$NH_2$ (SEQ ID NO: 24)
Gly-His-Arg-Pro-Leu-Asp-Lys-Lys-Lys-Glu-Glu-Ala-Pro-Ser-Leu-Arg-Pro-Ala-Pro-Pro-Pro-Ile-Ser-Gly-Gly-Gly-Tyr-Arg-$NH_2$ (SEQ ID NO: 25)
Gly-His-Arg-Pro-Leu-Asp-Lys-Lys-Arg-Glu-Glu-Gly-Pro-Ser-Leu-Arg-Pro-Ala-Pro-Pro-Pro-Ile-Ser-Gly-Gly-Gly-Tyr-Arg-$NH_2$ (SEQ ID NO: 26)
Gly-His-Arg-Pro-Leu-Asp-Lys-Lys-Arg-Glu-Glu-Ala-Pro-Leu-Leu-Arg-Pro-Ala-Pro-Pro-Pro-Ile-Ser-Gly-Gly-Gly-Tyr-Arg-$NH_2$ (SEQ ID NO: 27)
Gly-His-Arg-Pro-Leu-Asp-Lys-Lys-Arg-Glu-Glu-Ala-Pro-Ser-Leu-Lys-Pro-Ala-Pro-Pro-Pro-Ile-Ser-Gly-Gly-Gly-Tyr-Arg-$NH_2$ (SEQ ID NO: 28)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ala-Gly-Gly-Gly-Tyr-Arg-$NH_2$ (SEQ ID NO: 29)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ala-Ala-Gly-Gly-Tyr-Arg-$NH_2$ (SEQ ID NO: 30)
Gly-His-Arg-Pro-Ile-Asp-Lys-Arg-Arg-Glu-Glu-Ala-Pro-Ser-Ile-Arg-Pro-Ala-Pro-Pro-Pro-Ile-Ala-Gly-Gly-Gly-Tyr-Arg-$NH_2$

The following were prepared as in Example 2:

(SEQ ID NO: 31)
Gly-His-Arg-Pro-Ile-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-succinimido-$PEG_{20K}$)OH (SEQ ID NO: 32)
Gly-His-Arg-Pro-Leu-Asp-Arg-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-succinimido-$PEG_{10K}$)OH -continued (SEQ ID NO: 33)
Gly-His-Arg-Pro-Leu-Asp-Lys-Lys-Arg-Glu-Asp-Ala-Pro-Ser-Leu-Arg-Pro-Ala-Pro-Pro-Pro-Ile-Ser-Gly-Gly-Gly-Tyr-Arg-Cys-(S-succinimido-$PEG_{20K}$)OH (SEQ ID NO: 34)
Gly-His-Arg-Pro-Leu-Asp-Lys-Lys-Arg-Glu-Glu-Ala-Pro-Ala-Leu-Arg-Pro-Ala-Pro-Pro-Pro-Ile-Ser-Gly-Gly-Gly-Tyr-Arg-Cys-(S-succinimido-$PEG_{20K}$)OH (SEQ ID NO: 35)
Gly-His-Arg-Pro-Leu-Asp-Lys-Lys-Arg-Glu-Glu-Ala-Pro-Ala-Leu-Arg-Pro-Ala-Pro-Pro-Pro-Ile-Ala-Gly-Gly-Gly-Tyr-Arg-Cys-(S-succinimido-$PEG_{20K}$)OH (SEQ ID NO: 36)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-succinimido-$PEG_{10K}$)OH (SEQ ID NO: 37)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-succinimido-$PEG_{20K}$)OH (SEQ ID NO: 38)
Gly-His-Arg-Pro-Leu-Asp-Lys-Lys-Arg-Glu-Glu-Ala-Pro-Ser-Ile-Arg-Pro-Ala-Pro-Pro-Pro-Ile-Ser-Gly-Gly-Gly-Tyr-Arg-Cys-(S-succinimido-$PEG_{20K}$)OH The following were prepared as in Example 3:

(SEQ ID NO: 39)
Gly-His-Arg-Pro-Ile-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-succinimido-$PEG_{20K}$)amide (SEQ ID NO: 40)
Gly-His-Arg-Pro-Leu-Asp-Arg-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-succinimido-$PEG_{10K}$)amide (SEQ ID NO: 41)
Gly-His-Arg-Pro-Leu-Asp-Lys-Lys-Arg-Glu-Asp-Ala-Pro-Ser-Leu-Arg-Pro-Ala-Pro-Pro-Pro-Ile-Ser-Gly-Gly-Gly-Tyr-Arg-Cys-(S-succinimido-$PEG_{20K}$)amide (SEQ ID NO: 42)
Gly-His-Arg-Pro-Leu-Asp-Lys-Lys-Arg-Glu-Glu-Ala-Pro-Ala-Leu-Arg-Pro-Ala-Pro-Pro-Pro-Ile-Ser-Gly-Gly-Gly-Tyr-Arg-Cys-(S-succinimido-$PEG_{20K}$)amide (SEQ ID NO: 43)
Gly-His-Arg-Pro-Leu-Asp-Lys-Lys-Arg-Glu-Glu-Ala-Pro-Ala-Leu-Arg-Pro-Ala-Pro-Pro-Pro-Ile-Ala-Gly-Gly-Gly-Tyr-Arg-Cys-(S-succinimido-$PEG_{20K}$)amide (SEQ ID NO: 44)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-succinimido-$PEG_{10K}$)amide (SEQ ID NO: 45)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-succinimido-$PEG_{20K}$)amide (SEQ ID NO: 46)
Gly-His-Arg-Pro-Leu-Asp-Lys-Lys-Arg-Glu-Glu-Ala-Pro-Ser-Ile-Arg-Pro-Ala-Pro-Pro-Pro-Ile-Ser-Gly-Gly-Gly-Tyr-Arg-Cys-(S-succinimido-$PEG_{20K}$)amide

EXAMPLE 7

The biological effect of the compound of Example 1 was established in a model of LPS-induced pneumonitis. C57 Black mice were randomized in two groups of 6 animals each and treated as follows:

Group 1 received 100 ng/kg LPS intranasally, immediately after the administration of LPS the mice received 4.8 mg/kg of the agent of Example 1 (dissolved in 100 µl NaCl) i.p., a second dose followed 60 min after the administration of LPS.

Group 2 received 100 ng/kg LPS intranasally, immediately after the administration of LPS the mice received 100 µl NaCl i.p., 60 min after the LPS admininistration the mice again received 100 µl NaCl i.p. 6 hours after the application of LPS all groups were submitted to a bronchioalveolar lavage and the lungs were removed. From the lavage liquids the number of neutrophils (PMN) was determined. This brought the following results:

EXAMPLE 8

The biological effect of the compound of Example 3 was established in a model of Dengue virus infection in mice. 5-week-old male BALB/c mice were divided into 2 groups. All animals were infected subcutaneously with a mouse-adapted Dengue virus (DEN-2, strain P23085 at a dose of 1-2 $LD_{50}$. 15 mice received 0.1 ml of 0.8% saline as intramuscular injection (control). The treated animals received 4.8 mg/kg/day of the agent of Example 3 as an intramuscular injection (diluted in 0.1 ml of 0.8% saline) once a day for 5 days, starting on day 3 after the virus infection.

At the end of the treatment period (day 10) the survival rates were compared.

The following results were obtained:

| | Mortality | Percentage | |
|---|---|---|---|
| Control | 8/15 | 47% | |
| Example 3 | 0/10 | 0% | $p < 0.05$ |

EXAMPLE 9

(SEQ ID NO: 47)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-$CH_2$-CO-NH-$PEG_{20K}$)-OH

The synthesis of the monomeric peptide is carried analogically to Example 1, Tentagel of (Rapp Polymere) being used as resin support here with FMOC-Cys(Trt) as the first amino acid.

Following cleavage and purification of the peptide reaction is carried out with a suitable excess of Br—$CH_2$—CO—NH-$PEG_{20}$ K. Following recovery purification is carried out on Kromasil RP-18, and the identity of the product is confirmed by MALDI-MS.

EXAMPLE 10

(SEQ ID NO: 48)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Cys-(S-$CH_2$-CO-NH-$PEG_{20K}$)-amide 100 mg Tentagel-S-RAM (Rapp-Polymere) at a load of 0.24 mmol/g are transferred to a commercially available peptide synthesis device (PSMM(Shimadzu)), wherein the peptide sequence is constructed step-by-step according to the carbodiimide/HOBt method.

The FMOC-amino acid derivatives are pre-activated by adding a 5-fold equimolar excess of di-isopropy-carbodiimide (DIC), di-isopropy-ethylamine (DIPEA) und hydroxybenzotriazole (HOBt) and, following their transfer into the reaction vessel, mixed with the resin support for 30 minutes. Washing steps are carried out by 5 additions of 900 µl DMF and thorough mixing for 1 minute. Cleavage steps are carried out by the addition of 3×900 µl 30% piperidine in DMF and thorough mixing for 4 minutes.

Removal of the individual reaction and wash solutions is effected by forcing the solutions through the bottom frit of the reaction vessel.

The amino acid derivatives FMOC-Ala, FMOC-Arg(Pbf), FMOC-Asp, FMOC-Gly, FMOC-His(Trt), FMOC-Ile, FMOC-Leu, FMOC-Lys(BOC), FMOC-Pro, FMOC-Ser (tBu), FMOC-Cys(Trt) and FMOC-Tyr(tBu) (Orpegen) are employed.

Following cleavage and purification of the peptide reaction is carried out with a suitable excess of Br—$CH_2$—CO—NH-$PEG_{20}$ K. Following recovery purification is carried out on Kromasil RP-18, and the identity of the product is confirmed by MALDI-MS.

EXAMPLE 11

(SEQ ID NO: 49)
Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Cys-(S-$CH_2$-CO-NH-$PEG_{20K}$)-Gly-Tyr-Arg-amide 100 mg Tentagel-S-RAM (Rapp-Polymere) at a charge of 0.24 mmol/g are transferred to a commercially available peptide synthesis device (PSMM(Shimadzu)), wherein the peptide sequence is constructed step-by-step according to the carbodiimide/HOBt method.

The FMOC-amino acid derivatives are pre-activated by adding a 5-fold equimolar excess of di-isopropy-carbodiimide (DIC), di-isopropy-ethylamine (DIPEA) und hydroxybenzotriazole (HOBt) and, following their transfer into the reaction vessel, mixed with the resin support for 30 minutes. Washing steps are carried out by 5 additions of 900 µl DMF and thorough mixing for 1 minute. Cleavage steps are carried out by the addition of 3×900 µl 30% piperidine in DMF and thorough mixing for 4 minutes.

Removal of the individual reaction and wash solutions is effected by forcing the solutions through the bottom frit of the reaction vessel.

The amino acid derivatives FMOC-Ala, FMOC-Arg(Pbf), FMOC-Asp, FMOC-Gly, FMOC-His(Trt), FMOC-Ile, FMOC-Leu, FMOC-Lys(BOC), FMOC-Pro, FMOC-Ser (tBu), FMOC-Cys(Trt) and FMOC-Tyr(tBu) (Orpegen) are employed.

When synthesis is completed the peptide resin is dried. The peptide amide is subsequently cleaved by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20. The peptide thus obtained is reacted with O-(iodoacetyl)-N-hydroxysuccinimide, followed by amino-ethyloxi-$PEG_{20k}$.

After recovery, purification by means of gel chromatography and lyophilisation a pure product is obtained, the identity of which is confirmed by MALDI-MS.

EXAMPLE 12

(SEQ ID NO: 50)
Gly-His-Arg-Pro-Leu-Asp-Lys-Lys-Arg-Glu-Glu-Ala-
Pro-Ser-Leu-Arg-Pro-Ala-Pro-Pro-Pro-Ile-Ser-Gly-
Cys-(S-$CH_2$-CO-NH-$PEG_{20K}$)-Gly-Tyr-Arg-amide It is obtained as in Example 11, the sequence of protected amino acids being appropriately altered.

The following were produced as in Example 9:

(SEQ ID NO: 51)
Gly-His-Arg-Pro-Ile-Asp-Lys-Lys-Arg-Glu-Glu-Ala-
Pro-Ser-Leu-Arg-Pro-Ala-Pro-Pro-Pro-Ile-Ser-Gly-
Gly-Gly-Tyr-Arg-Cys-(S-$CH_2$-CO-NH-$PEG_{20K}$)OH (SEQ ID NO: 52)
Gly-His-Arg-Pro-Leu-Asp-Arg-Lys-Arg-Glu-Glu-Ala-
Pro-Ser-Leu-Arg-Pro-Ala-Pro-Pro-Pro-Ile-Ser-Gly-
Gly-Gly-Tyr-Arg-Cys-(S-$CH_2$-CO-NH-$PEG_{10K}$)OH (SEQ ID NO: 53)
Gly-His-Arg-Pro-Leu-Asp-Lys-Lys-Arg-Glu-Asp-Ala-
Pro-Ser-Leu-Arg-Pro-Ala-Pro-Pro-Pro-Ile-Ser-Gly-
Gly-Gly-Tyr-Arg-Cys-(S-$CH_2$-CO-NH-$PEG_{20K}$)OH (SEQ ID NO: 54)
Gly-His-Arg-Pro-Leu-Asp-Lys-Lys-Arg-Glu-Glu-Ala-
Pro-Ala-Leu-Arg-Pro-Ala-Pro-Pro-Pro-Ile-Ser-Gly-
Gly-Gly-Tyr-Arg-Cys-(S-$CH_2$-CO-NH-$PEG_{20K}$)OH (SEQ ID NO: 55)
Gly-His-Arg-Pro-Leu-Asp-Lys-Lys-Arg-Glu-Glu-Ala-
Pro-Ala-Leu-Arg-Pro-Ala-Pro-Pro-Pro-Ile-Ala-Gly-
Gly-Gly-Tyr-Arg-Cys-(S-$CH_2$-CO-NH-$PEG_{20K}$)OH

-continued (SEQ ID NO: 56)
Gly-His-Arg-Pro-Leu-Asp-Lys-Lys-Arg-Glu-Glu-Ala-
Pro-Ser-Leu-Arg-Pro-Ala-Pro-Pro-Pro-Ile-Ser-Gly-
Gly-Gly-Tyr-Arg-Cys-(S-$CH_2$-CO-NH-$PEG_{10K}$)OH (SEQ ID NO: 57)
Gly-His-Arg-Pro-Leu-Asp-Lys-Lys-Arg-Glu-Glu-Ala-
Pro-Ser-Leu-Arg-Pro-Ala-Pro-Pro-Pro-Ile-Ser-Gly-
Gly-Gly-Tyr-Arg-Cys-(S-$CH_2$-CO-NH-$PEG_{20K}$)OH (SEQ ID NO: 58)
Gly-His-Arg-Pro-Leu-Asp-Lys-Lys-Arg-Glu-Glu-Ala-
Pro-Ser-Ile-Arg-Pro-Ala-Pro-Pro-Pro-Ile-Ser-Gly-
Gly-Gly-Tyr-Arg-Cys-(S-$CH_2$-CO-NH-$PEG_{20K}$)OH The following were produced as in Example 10:

(SEQ ID NO: 59)
Gly-His-Arg-Pro-Ile-Asp-Lys-Lys-Arg-Glu-Glu-Ala-
Pro-Ser-Leu-Arg-Pro-Ala-Pro-Pro-Pro-Ile-Ser-Gly-
Gly-Gly-Tyr-Arg-Cys-(S-$CH_2$-CO-NH-$PEG_{20K}$)amide (SEQ ID NO: 60)
Gly-His-Arg-Pro-Leu-Asp-Arg-Lys-Arg-Glu-Glu-Ala-
Pro-Ser-Leu-Arg-Pro-Ala-Pro-Pro-Pro-Ile-Ser-Gly-
Gly-Gly-Tyr-Arg-Cys-(S-$CH_2$-CO-NH-$PEG_{10K}$)amide (SEQ ID NO: 61)
Gly-His-Arg-Pro-Leu-Asp-Lys-Lys-Arg-Glu-Asp-Ala-
Pro-Ser-Leu-Arg-Pro-Ala-Pro-Pro-Pro-Ile-Ser-Gly-
Gly-Gly-Tyr-Arg-Cys-(S-$CH_2$-CO-NH-$PEG_{20K}$)amide (SEQ ID NO: 62)
Gly-His-Arg-Pro-Leu-Asp-Lys-Lys-Arg-Glu-Glu-Ala-
Pro-Ala-Leu-Arg-Pro-Ala-Pro-Pro-Pro-Ile-Ser-Gly-
Gly-Gly-Tyr-Arg-Cys-(S-$CH_2$-CO-NH-$PEG_{20K}$)amide (SEQ ID NO: 63)
Gly-His-Arg-Pro-Leu-Asp-Lys-Lys-Arg-Glu-Glu-Ala-
Pro-Ala-Leu-Arg-Pro-Ala-Pro-Pro-Pro-Ile-Ala-Gly-
Gly-Gly-Tyr-Arg-Cys-(S-$CH_2$-CO-NH-$PEG_{20K}$)amide (SEQ ID NO: 64)
Gly-His-Arg-Pro-Leu-Asp-Lys-Lys-Arg-Glu-Glu-Ala-
Pro-Ser-Leu-Arg-Pro-Ala-Pro-Pro-Pro-Ile-Ser-Gly-
Gly-Gly-Tyr-Arg-Cys-(S-$CH_2$-CO-NH-$PEG_{10K}$)amide (SEQ ID NO: 65)
Gly-His-Arg-Pro-Leu-Asp-Lys-Lys-Arg-Glu-Glu-Ala-
Pro-Ser-Leu-Arg-Pro-Ala-Pro-Pro-Pro-Ile-Ser-Gly-
Gly-Gly-Tyr-Arg-Cys-(S-$CH_2$-CO-NH-$PEG_{20K}$)amide (SEQ ID NO: 66)
Gly-His-Arg-Pro-Leu-Asp-Lys-Lys-Arg-Glu-Glu-Ala-
Pro-Ser-Ile-Arg-Pro-Ala-Pro-Pro-Pro-Ile-Ser-Gly-
Gly-Gly-Tyr-Arg-Cys-(S-$CH_2$-CO-NH-$PEG_{20K}$)amide

SEQUENCE LISTING

```
<160> NUMBER OF SEQ ID NOS: 67

<210> SEQ ID NO 1
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MISC_FEATURE
<222> LOCATION: (5)..(5)
<223> OTHER INFORMATION: Xaa can be any genetically encoded amino acid
<220> FEATURE:
```

-continued

```
<221> NAME/KEY: MISC_FEATURE
<222> LOCATION: (6)..(6)
<223> OTHER INFORMATION: Xaa can be any genetically encoded amino acid
<220> FEATURE:
<221> NAME/KEY: MISC_FEATURE
<222> LOCATION: (7)..(7)
<223> OTHER INFORMATION: Xaa can be any genetically encoded amino acid
<220> FEATURE:
<221> NAME/KEY: MISC_FEATURE
<222> LOCATION: (8)..(8)
<223> OTHER INFORMATION: Xaa can be any genetically encoded amino acid
<220> FEATURE:
<221> NAME/KEY: MISC_FEATURE
<222> LOCATION: (9)..(9)
<223> OTHER INFORMATION: Xaa can be any genetically encoded amino acid
<220> FEATURE:
<221> NAME/KEY: MISC_FEATURE
<222> LOCATION: (10)..(10)
<223> OTHER INFORMATION: Xaa can be any genetically encoded amino acid
<220> FEATURE:
<221> NAME/KEY: MISC_FEATURE
<222> LOCATION: (11)..(11)
<223> OTHER INFORMATION: Xaa can be any genetically encoded amino acid
<220> FEATURE:
<221> NAME/KEY: MISC_FEATURE
<222> LOCATION: (12)..(12)
<223> OTHER INFORMATION: Xaa can be any genetically encoded amino acid
<220> FEATURE:
<221> NAME/KEY: MISC_FEATURE
<222> LOCATION: (14)..(14)
<223> OTHER INFORMATION: Xaa can be any genetically encoded amino acid
<220> FEATURE:
<221> NAME/KEY: MISC_FEATURE
<222> LOCATION: (15)..(15)
<223> OTHER INFORMATION: Xaa can be any genetically encoded amino acid
<220> FEATURE:
<221> NAME/KEY: MISC_FEATURE
<222> LOCATION: (16)..(16)
<223> OTHER INFORMATION: Xaa can be any genetically encoded amino acid
<220> FEATURE:
<221> NAME/KEY: MISC_FEATURE
<222> LOCATION: (18)..(18)
<223> OTHER INFORMATION: Xaa can be any genetically encoded amino acid
<220> FEATURE:
<221> NAME/KEY: MISC_FEATURE
<222> LOCATION: (22)..(22)
<223> OTHER INFORMATION: Xaa can be any genetically encoded amino acid
<220> FEATURE:
<221> NAME/KEY: MISC_FEATURE
<222> LOCATION: (23)..(23)
<223> OTHER INFORMATION: Xaa can be any genetically encoded amino acid
<220> FEATURE:
<221> NAME/KEY: MISC_FEATURE
<222> LOCATION: (24)..(24)
<223> OTHER INFORMATION: Xaa can be any genetically encoded amino acid
<220> FEATURE:
<221> NAME/KEY: MISC_FEATURE
<222> LOCATION: (25)..(25)
<223> OTHER INFORMATION: Xaa can be any genetically encoded amino acid
<220> FEATURE:
<221> NAME/KEY: MISC_FEATURE
<222> LOCATION: (28)..(28)
<223> OTHER INFORMATION: amino acid optionally modified as includes OR1
      with R1 = hydrogen or (C1-C10)-alkyl, or NR2R3, R2 and R3 being
      identical or different and denoting hydrogen, (C1-C10)-alkyl,
      or -PEG5-60K which is linked to the N atom via a spacer

<400> SEQUENCE: 1

Gly His Arg Pro Xaa Xaa Xaa Xaa Xaa Xaa Xaa Xaa Pro Xaa Xaa Xaa
1               5                   10                  15

Pro Xaa Pro Pro Pro Xaa Xaa Xaa Xaa Gly Tyr Arg
            20                  25


<210> SEQ ID NO 2
<211> LENGTH: 29
<212> TYPE: PRT
```

-continued

<213> ORGANISM: Artificial Sequence
<220> FEATURE:
<223> OTHER INFORMATION: Synthesized peptide derivative of Bbeta (15-28)
fibrin fragment
<220> FEATURE:
<221> NAME/KEY: MISC_FEATURE
<222> LOCATION: (5)..(5)
<223> OTHER INFORMATION: Xaa can be any genetically encoded amino acid
<220> FEATURE:
<221> NAME/KEY: MISC_FEATURE
<222> LOCATION: (6)..(6)
<223> OTHER INFORMATION: Xaa can be any genetically encoded amino acid
<220> FEATURE:
<221> NAME/KEY: MISC_FEATURE
<222> LOCATION: (7)..(7)
<223> OTHER INFORMATION: Xaa can be any genetically encoded amino acid
<220> FEATURE:
<221> NAME/KEY: MISC_FEATURE
<222> LOCATION: (8)..(8)
<223> OTHER INFORMATION: Xaa can be any genetically encoded amino acid
<220> FEATURE:
<221> NAME/KEY: MISC_FEATURE
<222> LOCATION: (9)..(9)
<223> OTHER INFORMATION: Xaa can be any genetically encoded amino acid
<220> FEATURE:
<221> NAME/KEY: MISC_FEATURE
<222> LOCATION: (10)..(10)
<223> OTHER INFORMATION: Xaa can be any genetically encoded amino acid
<220> FEATURE:
<221> NAME/KEY: MISC_FEATURE
<222> LOCATION: (11)..(11)
<223> OTHER INFORMATION: Xaa can be any genetically encoded amino acid
<220> FEATURE:
<221> NAME/KEY: MISC_FEATURE
<222> LOCATION: (12)..(12)
<223> OTHER INFORMATION: Xaa can be any genetically encoded amino acid
<220> FEATURE:
<221> NAME/KEY: MISC_FEATURE
<222> LOCATION: (14)..(14)
<223> OTHER INFORMATION: Xaa can be any genetically encoded amino acid
<220> FEATURE:
<221> NAME/KEY: MISC_FEATURE
<222> LOCATION: (15)..(15)
<223> OTHER INFORMATION: Xaa can be any genetically encoded amino acid
<220> FEATURE:
<221> NAME/KEY: MISC_FEATURE
<222> LOCATION: (16)..(16)
<223> OTHER INFORMATION: Xaa can be any genetically encoded amino acid
<220> FEATURE:
<221> NAME/KEY: MISC_FEATURE
<222> LOCATION: (18)..(18)
<223> OTHER INFORMATION: Xaa can be any genetically encoded amino acid
<220> FEATURE:
<221> NAME/KEY: MISC_FEATURE
<222> LOCATION: (22)..(22)
<223> OTHER INFORMATION: Xaa can be any genetically encoded amino acid
<220> FEATURE:
<221> NAME/KEY: MISC_FEATURE
<222> LOCATION: (23)..(23)
<223> OTHER INFORMATION: Xaa can be any genetically encoded amino acid
<220> FEATURE:
<221> NAME/KEY: MISC_FEATURE
<222> LOCATION: (24)..(24)
<223> OTHER INFORMATION: Xaa can be any genetically encoded amino acid
<220> FEATURE:
<221> NAME/KEY: MISC_FEATURE
<222> LOCATION: (25)..(25)
<223> OTHER INFORMATION: Xaa can be any genetically encoded amino acid
<220> FEATURE:
<221> NAME/KEY: MOD_RES
<222> LOCATION: (28)..(28)
<223> OTHER INFORMATION: AMIDATION
when amino acid at position 29 is absent, amino acid at position
28 is amidated
<220> FEATURE:
<221> NAME/KEY: MISC_FEATURE
<222> LOCATION: (28)..(28)
<223> OTHER INFORMATION: when amino acid at position 29 is absent, amino
acid at position 28 modified with -PEG5-60K which is linked to the -continued

```
      N atom via a spacer
<220> FEATURE:
<221> NAME/KEY: MISC_FEATURE
<222> LOCATION: (29)..(29)
<223> OTHER INFORMATION: Xaa denotes S, C, K, R or is absent
<220> FEATURE:
<221> NAME/KEY: MOD_RES
<222> LOCATION: (29)..(29)
<223> OTHER INFORMATION: AMIDATION
<220> FEATURE:
<221> NAME/KEY: MISC_FEATURE
<222> LOCATION: (29)..(29)
<223> OTHER INFORMATION: amino acid modified with -PEG5-60K which is
      linked to the N atom via a spacer

<400> SEQUENCE: 2

Gly His Arg Pro Xaa Xaa Xaa Xaa Xaa Xaa Xaa Xaa Pro Xaa Xaa Xaa
1               5                   10                  15

Pro Xaa Pro Pro Pro Xaa Xaa Xaa Xaa Gly Tyr Arg Xaa
            20                  25


<210> SEQ ID NO 3
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MISC_FEATURE
<222> LOCATION: (5)..(5)
<223> OTHER INFORMATION: Xaa can be any genetically encoded amino acid
<220> FEATURE:
<221> NAME/KEY: MISC_FEATURE
<222> LOCATION: (6)..(6)
<223> OTHER INFORMATION: Xaa can be any genetically encoded amino acid
<220> FEATURE:
<221> NAME/KEY: MISC_FEATURE
<222> LOCATION: (7)..(7)
<223> OTHER INFORMATION: Xaa can be any genetically encoded amino acid
<220> FEATURE:
<221> NAME/KEY: MISC_FEATURE
<222> LOCATION: (8)..(8)
<223> OTHER INFORMATION: Xaa can be any genetically encoded amino acid
<220> FEATURE:
<221> NAME/KEY: MISC_FEATURE
<222> LOCATION: (9)..(9)
<223> OTHER INFORMATION: Xaa can be any genetically encoded amino acid
<220> FEATURE:
<221> NAME/KEY: MISC_FEATURE
<222> LOCATION: (10)..(10)
<223> OTHER INFORMATION: Xaa can be any genetically encoded amino acid
<220> FEATURE:
<221> NAME/KEY: MISC_FEATURE
<222> LOCATION: (11)..(11)
<223> OTHER INFORMATION: Xaa can be any genetically encoded amino acid
<220> FEATURE:
<221> NAME/KEY: MISC_FEATURE
<222> LOCATION: (12)..(12)
<223> OTHER INFORMATION: Xaa can be any genetically encoded amino acid
<220> FEATURE:
<221> NAME/KEY: MISC_FEATURE
<222> LOCATION: (14)..(14)
<223> OTHER INFORMATION: Xaa can be any genetically encoded amino acid
<220> FEATURE:
<221> NAME/KEY: MISC_FEATURE
<222> LOCATION: (15)..(15)
<223> OTHER INFORMATION: Xaa can be any genetically encoded amino acid
<220> FEATURE:
<221> NAME/KEY: MISC_FEATURE
<222> LOCATION: (16)..(16)
<223> OTHER INFORMATION: Xaa can be any genetically encoded amino acid
<220> FEATURE:
<221> NAME/KEY: MISC_FEATURE
<222> LOCATION: (18)..(18)
<223> OTHER INFORMATION: Xaa can be any genetically encoded amino acid
```

-continued

```
<220> FEATURE:
<221> NAME/KEY: MISC_FEATURE
<222> LOCATION: (22)..(22)
<223> OTHER INFORMATION: Xaa can be any genetically encoded amino acid
<220> FEATURE:
<221> NAME/KEY: MISC_FEATURE
<222> LOCATION: (23)..(23)
<223> OTHER INFORMATION: Xaa can be any genetically encoded amino acid
<220> FEATURE:
<221> NAME/KEY: MISC_FEATURE
<222> LOCATION: (24)..(25)
<223> OTHER INFORMATION: one of the two residues being an amino acid
      from the group of C or K, which is linked to a residue Z-PEG5-60K
      via the heteroatom in the side chain and the other residue being
      any genetically encoded amino acid
<220> FEATURE:
<221> NAME/KEY: MISC_FEATURE
<222> LOCATION: (28)..(28)
<223> OTHER INFORMATION: amino acid optionally modified as includes OR1
      with R1 = hydrogen or (C1-C10)-alkyl, or NR2R3, R2 and R3 being
      identical or different and denoting hydrogen or (C1-C10)-alkyl

<400> SEQUENCE: 3

Gly His Arg Pro Xaa Xaa Xaa Xaa Xaa Xaa Xaa Xaa Pro Xaa Xaa Xaa
1               5                   10                  15

Pro Xaa Pro Pro Pro Xaa Xaa Xaa Xaa Gly Tyr Arg
            20                  25


<210> SEQ ID NO 4
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MISC_FEATURE
<222> LOCATION: (5)..(5)
<223> OTHER INFORMATION: Xaa denotes amino acid L, I, S, M or A
<220> FEATURE:
<221> NAME/KEY: MISC_FEATURE
<222> LOCATION: (6)..(6)
<223> OTHER INFORMATION: Xaa denotes amino acid E or D
<220> FEATURE:
<221> NAME/KEY: MISC_FEATURE
<222> LOCATION: (7)..(7)
<223> OTHER INFORMATION: Xaa denotes amino acid R or K
<220> FEATURE:
<221> NAME/KEY: MISC_FEATURE
<222> LOCATION: (8)..(8)
<223> OTHER INFORMATION: Xaa denotes amino acid R or K
<220> FEATURE:
<221> NAME/KEY: MISC_FEATURE
<222> LOCATION: (9)..(9)
<223> OTHER INFORMATION: Xaa denotes amino acid R or K
<220> FEATURE:
<221> NAME/KEY: MISC_FEATURE
<222> LOCATION: (10)..(10)
<223> OTHER INFORMATION: Xaa denotes amino acid E or D
<220> FEATURE:
<221> NAME/KEY: MISC_FEATURE
<222> LOCATION: (11)..(11)
<223> OTHER INFORMATION: Xaa denotes amino acid E or D
<220> FEATURE:
<221> NAME/KEY: MISC_FEATURE
<222> LOCATION: (12)..(12)
<223> OTHER INFORMATION: Xaa denotes amino acid A, G, S, or L
<220> FEATURE:
<221> NAME/KEY: MISC_FEATURE
<222> LOCATION: (14)..(14)
<223> OTHER INFORMATION: Xaa denotes amino acid L, I, S, M or A
<220> FEATURE:
<221> NAME/KEY: MISC_FEATURE
<222> LOCATION: (15)..(15)
<223> OTHER INFORMATION: Xaa denotes amino acid L, I, S, M or A
<220> FEATURE:
```

-continued

```
<221> NAME/KEY: MISC_FEATURE
<222> LOCATION: (16)..(16)
<223> OTHER INFORMATION: Xaa denotes amino acid R or K
<220> FEATURE:
<221> NAME/KEY: MISC_FEATURE
<222> LOCATION: (18)..(18)
<223> OTHER INFORMATION: Xaa denotes amino acid A, G, S, or L
<220> FEATURE:
<221> NAME/KEY: MISC_FEATURE
<222> LOCATION: (22)..(22)
<223> OTHER INFORMATION: Xaa denotes amino acid I, L or V
<220> FEATURE:
<221> NAME/KEY: MISC_FEATURE
<222> LOCATION: (23)..(23)
<223> OTHER INFORMATION: Xaa denotes amino acid L, I, S, M or A
<220> FEATURE:
<221> NAME/KEY: MISC_FEATURE
<222> LOCATION: (24)..(24)
<223> OTHER INFORMATION: Xaa can be any genetically encoded amino acid
<220> FEATURE:
<221> NAME/KEY: MISC_FEATURE
<222> LOCATION: (25)..(25)
<223> OTHER INFORMATION: Xaa can be any genetically encoded amino acid
<220> FEATURE:
<221> NAME/KEY: MISC_FEATURE
<222> LOCATION: (28)..(28)
<223> OTHER INFORMATION: amino acid optionally modified as includes OR1
      with R1 = hydrogen or (C1-C10)-alkyl, or NR2R3, R2 and R3 being
      identical or different and denoting hydrogen, (C1-C10)-alkyl,
      or -PEG5-60K which is linked to the N atom via a spacer

<400> SEQUENCE: 4

Gly His Arg Pro Xaa Xaa Xaa Xaa Xaa Xaa Xaa Xaa Pro Xaa Xaa Xaa
1               5                   10                  15

Pro Xaa Pro Pro Pro Xaa Xaa Xaa Xaa Gly Tyr Arg
            20                  25


<210> SEQ ID NO 5
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MISC_FEATURE
<222> LOCATION: (5)..(5)
<223> OTHER INFORMATION: Xaa denotes amino acid L, I, S, M or A
<220> FEATURE:
<221> NAME/KEY: MISC_FEATURE
<222> LOCATION: (6)..(6)
<223> OTHER INFORMATION: Xaa denotes amino acid E or D
<220> FEATURE:
<221> NAME/KEY: MISC_FEATURE
<222> LOCATION: (7)..(7)
<223> OTHER INFORMATION: Xaa denotes amino acid R or K
<220> FEATURE:
<221> NAME/KEY: MISC_FEATURE
<222> LOCATION: (8)..(8)
<223> OTHER INFORMATION: Xaa denotes amino acid R or K
<220> FEATURE:
<221> NAME/KEY: MISC_FEATURE
<222> LOCATION: (9)..(9)
<223> OTHER INFORMATION: Xaa denotes amino acid R or K
<220> FEATURE:
<221> NAME/KEY: MISC_FEATURE
<222> LOCATION: (10)..(10)
<223> OTHER INFORMATION: Xaa denotes amino acid E or D
<220> FEATURE:
<221> NAME/KEY: MISC_FEATURE
<222> LOCATION: (11)..(11)
<223> OTHER INFORMATION: Xaa denotes amino acid E or D
<220> FEATURE:
<221> NAME/KEY: MISC_FEATURE
<222> LOCATION: (12)..(12)
<223> OTHER INFORMATION: Xaa denotes amino acid A, G, S, or L
```

-continued

```
<220> FEATURE:
<221> NAME/KEY: MISC_FEATURE
<222> LOCATION: (14)..(14)
<223> OTHER INFORMATION: Xaa denotes amino acid L, I, S, M or A
<220> FEATURE:
<221> NAME/KEY: MISC_FEATURE
<222> LOCATION: (15)..(15)
<223> OTHER INFORMATION: Xaa denotes amino acid L, I, S, M or A
<220> FEATURE:
<221> NAME/KEY: MISC_FEATURE
<222> LOCATION: (16)..(16)
<223> OTHER INFORMATION: Xaa denotes amino acid R or K
<220> FEATURE:
<221> NAME/KEY: MISC_FEATURE
<222> LOCATION: (18)..(18)
<223> OTHER INFORMATION: Xaa denotes amino acid A, G, S, or L
<220> FEATURE:
<221> NAME/KEY: MISC_FEATURE
<222> LOCATION: (22)..(22)
<223> OTHER INFORMATION: Xaa denotes amino acid I, L or V
<220> FEATURE:
<221> NAME/KEY: MISC_FEATURE
<222> LOCATION: (23)..(23)
<223> OTHER INFORMATION: Xaa denotes amino acid L, I, S, M or A
<220> FEATURE:
<221> NAME/KEY: MISC_FEATURE
<222> LOCATION: (24)..(24)
<223> OTHER INFORMATION: Xaa can be any genetically encoded amino acid
<220> FEATURE:
<221> NAME/KEY: MISC_FEATURE
<222> LOCATION: (25)..(25)
<223> OTHER INFORMATION: Xaa can be any genetically encoded amino acid
<220> FEATURE:
<221> NAME/KEY: MOD_RES
<222> LOCATION: (28)..(28)
<223> OTHER INFORMATION: AMIDATION
      when amino acid at position 29 is absent, amino acid at position
      28 is amidated
<220> FEATURE:
<221> NAME/KEY: MISC_FEATURE
<222> LOCATION: (28)..(28)
<223> OTHER INFORMATION: when amino acid at position 29 is absent, amino
      acid at position 28 modified with -PEG5-60K which is linked to the
      N atom via a spacer
<220> FEATURE:
<221> NAME/KEY: MISC_FEATURE
<222> LOCATION: (29)..(29)
<223> OTHER INFORMATION: Xaa denotes S, C, K, R or is absent
<220> FEATURE:
<221> NAME/KEY: MOD_RES
<222> LOCATION: (29)..(29)
<223> OTHER INFORMATION: AMIDATION
<220> FEATURE:
<221> NAME/KEY: MISC_FEATURE
<222> LOCATION: (29)..(29)
<223> OTHER INFORMATION: amino acid modified with -PEG5-60K which is
      linked to the N atom via a spacer

<400> SEQUENCE: 5

Gly His Arg Pro Xaa Xaa Xaa Xaa Xaa Xaa Xaa Xaa Pro Xaa Xaa Xaa
1               5                   10                  15

Pro Xaa Pro Pro Pro Xaa Xaa Xaa Xaa Gly Tyr Arg Xaa
            20                  25


<210> SEQ ID NO 6
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MISC_FEATURE
<222> LOCATION: (5)..(5)
<223> OTHER INFORMATION: Xaa denotes amino acid L, I, S, M or A
<220> FEATURE:
```

-continued

```
<221> NAME/KEY: MISC_FEATURE
<222> LOCATION: (6)..(6)
<223> OTHER INFORMATION: Xaa denotes amino acid E or D
<220> FEATURE:
<221> NAME/KEY: MISC_FEATURE
<222> LOCATION: (7)..(7)
<223> OTHER INFORMATION: Xaa denotes amino acid R or K
<220> FEATURE:
<221> NAME/KEY: MISC_FEATURE
<222> LOCATION: (8)..(8)
<223> OTHER INFORMATION: Xaa denotes amino acid R or K
<220> FEATURE:
<221> NAME/KEY: MISC_FEATURE
<222> LOCATION: (9)..(9)
<223> OTHER INFORMATION: Xaa denotes amino acid R or K
<220> FEATURE:
<221> NAME/KEY: MISC_FEATURE
<222> LOCATION: (10)..(10)
<223> OTHER INFORMATION: Xaa denotes amino acid E or D
<220> FEATURE:
<221> NAME/KEY: MISC_FEATURE
<222> LOCATION: (11)..(11)
<223> OTHER INFORMATION: Xaa denotes amino acid E or D
<220> FEATURE:
<221> NAME/KEY: MISC_FEATURE
<222> LOCATION: (12)..(12)
<223> OTHER INFORMATION: Xaa denotes amino acid A, G, S, or L
<220> FEATURE:
<221> NAME/KEY: MISC_FEATURE
<222> LOCATION: (14)..(14)
<223> OTHER INFORMATION: Xaa denotes amino acid L, I, S, M or A
<220> FEATURE:
<221> NAME/KEY: MISC_FEATURE
<222> LOCATION: (15)..(15)
<223> OTHER INFORMATION: Xaa denotes amino acid L, I, S, M or A
<220> FEATURE:
<221> NAME/KEY: MISC_FEATURE
<222> LOCATION: (16)..(16)
<223> OTHER INFORMATION: Xaa denotes amino acid R or K
<220> FEATURE:
<221> NAME/KEY: MISC_FEATURE
<222> LOCATION: (18)..(18)
<223> OTHER INFORMATION: Xaa denotes amino acid A, G, S, or L
<220> FEATURE:
<221> NAME/KEY: MISC_FEATURE
<222> LOCATION: (22)..(22)
<223> OTHER INFORMATION: Xaa denotes amino acid I, L or V
<220> FEATURE:
<221> NAME/KEY: MISC_FEATURE
<222> LOCATION: (23)..(23)
<223> OTHER INFORMATION: Xaa denotes amino acid L, I, S, M or A
<220> FEATURE:
<221> NAME/KEY: MISC_FEATURE
<222> LOCATION: (24)..(25)
<223> OTHER INFORMATION: one of the two residues being an amino acid
      from the group of C or K, which is linked to a residue Z-PEG5-60K
      via the heteroatom in the side chain and the other residue being
      any genetically encoded amino acid
<220> FEATURE:
<221> NAME/KEY: MISC_FEATURE
<222> LOCATION: (28)..(28)
<223> OTHER INFORMATION: amino acid optionally modified as includes OR1
      with R1 = hydrogen or (C1-C10)-alkyl, or NR2R3, R2 and R3 being
      identical or different and denoting hydrogen or (C1-C10)-alkyl

<400> SEQUENCE: 6

Gly His Arg Pro Xaa Xaa Xaa Xaa Xaa Xaa Xaa Xaa Pro Xaa Xaa Xaa
1               5                   10                  15

Pro Xaa Pro Pro Pro Xaa Xaa Xaa Xaa Gly Tyr Arg
            20                  25


<210> SEQ ID NO 7
<211> LENGTH: 28
<212> TYPE: PRT
<213> ORGANISM: Artificial Sequence
<220> FEATURE:
```

-continued

<223> OTHER INFORMATION: Synthesized peptide derivative of Bbeta (15-28)
      fibrin fragment
<220> FEATURE:
<221> NAME/KEY: MISC_FEATURE
<222> LOCATION: (29)..(29)
<223> OTHER INFORMATION: amino acid optionally modified as includes OR1
      with R1 = hydrogen or (C1-C10)-alkyl, or NR2R3, R2 and R3 being
      identical or different and denoting hydrogen, (C1-C10)-alkyl,
      or -PEG5-60K which is linked to the N atom via a spacer

<400> SEQUENCE: 7

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg
            20                  25

<210> SEQ ID NO 8
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION
      when amino acid at position 29 is absent, amino acid at position
      28 is amidated
<220> FEATURE:
<221> NAME/KEY: MISC_FEATURE
<222> LOCATION: (28)..(28)
<223> OTHER INFORMATION: when amino acid at position 29 is absent, amino
      acid at position 28 modified with -PEG-5-60K which is linked to
      the N atom via a spacer
<220> FEATURE:
<221> NAME/KEY: MISC_FEATURE
<222> LOCATION: (29)..(29)
<223> OTHER INFORMATION: Xaa denotes S, C, K, R or is absent
<220> FEATURE:
<221> NAME/KEY: MOD_RES
<222> LOCATION: (29)..(29)
<223> OTHER INFORMATION: AMIDATION
<220> FEATURE:
<221> NAME/KEY: MISC_FEATURE
<222> LOCATION: (29)..(29)
<223> OTHER INFORMATION: amino acid modified with -PEG5-60K which is
      linked to the N atom via a spacer

<400> SEQUENCE: 8

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Xaa
            20                  25

<210> SEQ ID NO 9
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MISC_FEATURE
<222> LOCATION: (28)..(28)
<223> OTHER INFORMATION: when amino acid at position 29 is absent, amino
      acid at position 28 is modified with NR2R3, R2 and R3 being
      identical or different and being hydrogen or (C1-C10)-alkyl
<220> FEATURE:
<221> NAME/KEY: MISC_FEATURE
<222> LOCATION: (29)..(29)
<223> OTHER INFORMATION: Xaa is C or is absent
<220> FEATURE:

-continued

```
<221> NAME/KEY: MISC_FEATURE
<222> LOCATION: (29)..(29)
<223> OTHER INFORMATION: amino acid modified with
      (NR2R3)-(S-succinimido)-(PEG5-40K), R2 and R3 being identical or
      different and being hydrogen or (C1-C10)-alkyl and the succinimide
      residue being linked via C-atom 3 to the sulfur atom of the
      cysteine residue

<400> SEQUENCE: 9

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Xaa
            20                  25


<210> SEQ ID NO 10
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MISC_FEATURE
<222> LOCATION: (24)..(26)
<223> OTHER INFORMATION: two of the residues each are a glycine residue
      and the remaining one is a residue C-(S-succinimido)-(PEG5-40K),
      the succinimido residue being linked to the sulfur atom of the
      cysteine residue via C-atom 3
<220> FEATURE:
<221> NAME/KEY: MISC_FEATURE
<222> LOCATION: (28)..(28)
<223> OTHER INFORMATION: amino acid modified with NR2R3, R2 and R3 being
      identical or different and being hydrogen or (C1-C10)-alkyl

<400> SEQUENCE: 10

Gly His Arg Pro Leu Asp Lys Lys Arg Glu Glu Ala Pro Ser Leu Arg
1               5                   10                  15

Pro Ala Pro Pro Pro Ile Ser Xaa Xaa Xaa Tyr Arg
            20                  25


<210> SEQ ID NO 11
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MISC_FEATURE
<222> LOCATION: (24)..(26)
<223> OTHER INFORMATION: two of the residues each are a glycine residue
      and the remaining one is a residue K-(PEG5-40K), the PEG-residue
      being linked via the nitrogen atom in the side chain of the lysine
      residue
<220> FEATURE:
<221> NAME/KEY: MISC_FEATURE
<222> LOCATION: (28)..(28)
<223> OTHER INFORMATION: amino acid modified with NR2R3, R2 and R3 being
      identical or different and being hydrogen or (C1-C10)-alkyl

<400> SEQUENCE: 11

Gly His Arg Pro Leu Asp Lys Lys Arg Glu Glu Ala Pro Ser Leu Arg
1               5                   10                  15

Pro Ala Pro Pro Pro Ile Ser Xaa Xaa Xaa Tyr Arg
            20                  25


<210> SEQ ID NO 12
<211> LENGTH: 28
<212> TYPE: PRT
<213> ORGANISM: Artificial Sequence
```

-continued

```
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 12

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg
            20                  25


<210> SEQ ID NO 13
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for succinimido-PEG20K residue,
      the succinimido-PEG20K residue being linked to the sulfur atom of
      the cysteine residue

<400> SEQUENCE: 13

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Cys
            20                  25


<210> SEQ ID NO 14
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for succinimido-PEG20K residue,
      the succinimido-PEG20K residue being linked to the sulfur atom of
      the cysteine residue
<220> FEATURE:
<221> NAME/KEY: MOD_RES
<222> LOCATION: (29)..(29)
<223> OTHER INFORMATION: AMIDATION

<400> SEQUENCE: 14

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Cys
            20                  25


<210> SEQ ID NO 15
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (25)..(25)
<223> OTHER INFORMATION: binding site for succinimido-PEG20K residue,
      the succinimido-PEG20K residue being linked to the sulfur atom of
```

-continued

```
      the cysteine residue
<220> FEATURE:
<221> NAME/KEY: MOD_RES
<222> LOCATION: (28)..(28)
<223> OTHER INFORMATION: AMIDATION

<400> SEQUENCE: 15

Gly His Arg Pro Leu Asp Lys Lys Arg Glu Glu Ala Pro Ser Leu Arg
1               5                   10                  15

Pro Ala Pro Pro Pro Ile Ser Gly Cys Gly Tyr Arg
            20                  25


<210> SEQ ID NO 16
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (24)..(24)
<223> OTHER INFORMATION: binding site for succinimido-PEG20K residue,
      the succinimido-PEG20K residue being linked to the sulfur atom of
      the cysteine residue
<220> FEATURE:
<221> NAME/KEY: MOD_RES
<222> LOCATION: (28)..(28)
<223> OTHER INFORMATION: AMIDATION

<400> SEQUENCE: 16

Gly His Arg Pro Leu Asp Lys Lys Arg Glu Glu Ala Pro Ser Leu Arg
1               5                   10                  15

Pro Ala Pro Pro Pro Ile Ser Cys Gly Gly Tyr Arg
            20                  25


<210> SEQ ID NO 17
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (26)..(26)
<223> OTHER INFORMATION: binding site for S-succinimido-PEG20K residue,
      the succinimido-PEG20K residue being linked to the sulfur atom of
      the cysteine residue
<220> FEATURE:
<221> NAME/KEY: MOD_RES
<222> LOCATION: (28)..(28)
<223> OTHER INFORMATION: AMIDATION

<400> SEQUENCE: 17

Gly His Arg Pro Leu Asp Lys Lys Arg Glu Glu Ala Pro Ser Leu Arg
1               5                   10                  15

Pro Ala Pro Pro Pro Ile Ser Gly Gly Cys Tyr Arg
            20                  25


<210> SEQ ID NO 18
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
```

-continued

<223> OTHER INFORMATION: AMIDATION

<400> SEQUENCE: 18

Gly His Arg Pro Ile Asp Lys Lys Arg Glu Glu Ala Pro Ser Leu Arg
1               5                   10                  15

Pro Ala Pro Pro Pro Ile Ser Gly Gly Gly Tyr Arg
            20                  25

<210> SEQ ID NO 19
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 19

Gly His Arg Pro Ala Asp Lys Lys Arg Glu Glu Ala Pro Ser Leu Arg
1               5                   10                  15

Pro Ala Pro Pro Pro Ile Ser Gly Gly Gly Tyr Arg
            20                  25

<210> SEQ ID NO 20
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 20

Gly His Arg Pro Leu Asp Arg Lys Arg Glu Glu Ala Pro Ser Leu Arg
1               5                   10                  15

Pro Ala Pro Pro Pro Ile Ser Gly Gly Gly Tyr Arg
            20                  25

<210> SEQ ID NO 21
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 21

Gly His Arg Pro Leu Asp Lys Arg Arg Glu Glu Ala Pro Ser Leu Arg
1               5                   10                  15

Pro Ala Pro Pro Pro Ile Ser Gly Gly Gly Tyr Arg
            20                  25

<210> SEQ ID NO 22
<211> LENGTH: 28
<212> TYPE: PRT
<213> ORGANISM: Artificial Sequence
<220> FEATURE:

-continued

```
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 22

Gly His Arg Pro Leu Asp Lys Lys Arg Asp Glu Ala Pro Ser Leu Arg
1               5                   10                  15

Pro Ala Pro Pro Pro Ile Ser Gly Gly Gly Tyr Arg
            20                  25


<210> SEQ ID NO 23
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 23

Gly His Arg Pro Leu Asp Lys Lys Arg Glu Asp Ala Pro Ser Leu Arg
1               5                   10                  15

Pro Ala Pro Pro Pro Ile Ser Gly Gly Gly Tyr Arg
            20                  25


<210> SEQ ID NO 24
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 24

Gly His Arg Pro Leu Asp Lys Lys Lys Glu Glu Ala Pro Ser Leu Arg
1               5                   10                  15

Pro Ala Pro Pro Pro Ile Ser Gly Gly Gly Tyr Arg
            20                  25


<210> SEQ ID NO 25
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 25

Gly His Arg Pro Leu Asp Lys Lys Arg Glu Glu Gly Pro Ser Leu Arg
1               5                   10                  15

Pro Ala Pro Pro Pro Ile Ser Gly Gly Gly Tyr Arg
            20                  25
```

-continued

```
<210> SEQ ID NO 26
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 26

Gly His Arg Pro Leu Asp Lys Lys Arg Glu Glu Ala Pro Leu Leu Arg
1               5                   10                  15

Pro Ala Pro Pro Pro Ile Ser Gly Gly Gly Tyr Arg
            20                  25


<210> SEQ ID NO 27
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 27

Gly His Arg Pro Leu Asp Lys Lys Arg Glu Glu Ala Pro Ser Leu Lys
1               5                   10                  15

Pro Ala Pro Pro Pro Ile Ser Gly Gly Gly Tyr Arg
            20                  25


<210> SEQ ID NO 28
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 28

Gly His Arg Pro Leu Asp Lys Lys Arg Glu Glu Ala Pro Ser Leu Arg
1               5                   10                  15

Pro Ala Pro Pro Pro Ile Ala Gly Gly Gly Tyr Arg
            20                  25


<210> SEQ ID NO 29
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 29

Gly His Arg Pro Leu Asp Lys Lys Arg Glu Glu Ala Pro Ser Leu Arg
1               5                   10                  15
```

-continued

```
Pro Ala Pro Pro Pro Ile Ala Ala Gly Gly Tyr Arg
            20                  25


<210> SEQ ID NO 30
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: MOD_RES
<222> LOCATION: (28)..(28)
<223> OTHER INFORMATION: AMIDATION

<400> SEQUENCE: 30

Gly His Arg Pro Ile Asp Lys Arg Arg Glu Glu Ala Pro Ser Ile Arg
1               5                   10                  15

Pro Ala Pro Pro Pro Ile Ala Gly Gly Gly Tyr Arg
            20                  25


<210> SEQ ID NO 31
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for succinimido-PEG20K residue,
      the succinimido-PEG20K residue being linked to the sulfur atom of
      the cysteine residue

<400> SEQUENCE: 31

Gly His Arg Pro Ile Asp Lys Lys Arg Glu Glu Ala Pro Ser Leu Arg
1               5                   10                  15

Pro Ala Pro Pro Pro Ile Ser Gly Gly Gly Tyr Arg Cys
            20                  25


<210> SEQ ID NO 32
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for succinimido-PEG10K residue,
      the succinimido-PEG10K residue being linked to the sulfur atom of
      the cysteine residue

<400> SEQUENCE: 32

Gly His Arg Pro Leu Asp Arg Lys Arg Glu Glu Ala Pro Ser Leu Arg
1               5                   10                  15

Pro Ala Pro Pro Pro Ile Ser Gly Gly Gly Tyr Arg Cys
            20                  25


<210> SEQ ID NO 33
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
```

-continued

```
<220> FEATURE:
<221> NAME/KEY: BINDING
<222> LOCATION: (29)..(29)
<223> OTHER INFORMATION: binding site for succinimido-PEG20K residue,
      the succinimido-PEG20K residue being linked to the sulfur atom of
      the cysteine residue

<400> SEQUENCE: 33

Gly His Arg Pro Leu Asp Lys Lys Arg Glu Asp Ala Pro Ser Leu Arg
1               5                   10                  15

Pro Ala Pro Pro Pro Ile Ser Gly Gly Gly Tyr Arg Cys
            20                  25


<210> SEQ ID NO 34
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for succinimido-PEG20K residue,
      the succinimido-PEG20K residue being linked to the sulfur atom of
      the cysteine residue

<400> SEQUENCE: 34

Gly His Arg Pro Leu Asp Lys Lys Arg Glu Glu Ala Pro Ala Leu Arg
1               5                   10                  15

Pro Ala Pro Pro Pro Ile Ser Gly Gly Gly Tyr Arg Cys
            20                  25


<210> SEQ ID NO 35
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for succinimido-PEG20K residue,
      the succinimido-PEG20K residue being linked to the sulfur atom of
      the cysteine residue

<400> SEQUENCE: 35

Gly His Arg Pro Leu Asp Lys Lys Arg Glu Glu Ala Pro Ala Leu Arg
1               5                   10                  15

Pro Ala Pro Pro Pro Ile Ala Gly Gly Gly Tyr Arg Cys
            20                  25


<210> SEQ ID NO 36
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for succinimido-PEG10K residue,
      the succinimido-PEG10K residue being linked to the sulfur atom of
      the cysteine residue

<400> SEQUENCE: 36

Gly His Arg Pro Leu Asp Lys Lys Arg Glu Glu Ala Pro Ser Leu Arg
```

-continued 1 5 10 15

Pro Ala Pro Pro Pro Ile Ser Gly Gly Gly Tyr Arg Cys
20 25

<210> SEQ ID NO 37
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for succinimido-PEG20K residue, the succinimido-PEG20K residue being linked to the sulfur atom of the cysteine residue

<400> SEQUENCE: 37

Gly His Arg Pro Leu Asp Lys Lys Arg Glu Glu Ala Pro Ser Leu Arg
1 5 10 15

Pro Ala Pro Pro Pro Ile Ser Gly Gly Gly Tyr Arg Cys
20 25

<210> SEQ ID NO 38
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for succinimido-PEG20K residue, the succinimido-PEG20K residue being linked to the sulfur atom of the cysteine residue

<400> SEQUENCE: 38

Gly His Arg Pro Leu Asp Lys Lys Arg Glu Glu Ala Pro Ser Ile Arg
1 5 10 15

Pro Ala Pro Pro Pro Ile Ser Gly Gly Gly Tyr Arg Cys
20 25

<210> SEQ ID NO 39
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for succinimido-PEG20K residue, the succinimido-PEG20K residue being linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 39

Gly His Arg Pro Ile Asp Lys Lys Arg Glu Glu Ala Pro Ser Leu Arg
1 5 10 15

Pro Ala Pro Pro Pro Ile Ser Gly Gly Gly Tyr Arg Cys
20 25

-continued

```
<210> SEQ ID NO 40
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for succinimido-PEG10K residue,
      the succinimido-PEG10K residue being linked to the sulfur atom of
      the cysteine residue
<220> FEATURE:
<221> NAME/KEY: MOD_RES
<222> LOCATION: (29)..(29)
<223> OTHER INFORMATION: AMIDATION

<400> SEQUENCE: 40

Gly His Arg Pro Leu Asp Arg Lys Arg Glu Glu Ala Pro Ser Leu Arg
1               5                   10                  15

Pro Ala Pro Pro Pro Ile Ser Gly Gly Gly Tyr Arg Cys
            20                  25


<210> SEQ ID NO 41
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for succinimido-PEG20K residue,
      the succinimido-PEG20K residue being linked to the sulfur atom of
      the cysteine residue
<220> FEATURE:
<221> NAME/KEY: MOD_RES
<222> LOCATION: (29)..(29)
<223> OTHER INFORMATION: AMIDATION

<400> SEQUENCE: 41

Gly His Arg Pro Leu Asp Lys Lys Arg Glu Asp Ala Pro Ser Leu Arg
1               5                   10                  15

Pro Ala Pro Pro Pro Ile Ser Gly Gly Gly Tyr Arg Cys
            20                  25


<210> SEQ ID NO 42
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for succinimido-PEG20K residue,
      the succinimido-PEG20K residue being linked to the sulfur atom of
      the cysteine residue
<220> FEATURE:
<221> NAME/KEY: MOD_RES
<222> LOCATION: (29)..(29)
<223> OTHER INFORMATION: AMIDATION

<400> SEQUENCE: 42

Gly His Arg Pro Leu Asp Lys Lys Arg Glu Glu Ala Pro Ala Leu Arg
1               5                   10                  15

Pro Ala Pro Pro Pro Ile Ser Gly Gly Gly Tyr Arg Cys
            20                  25
```

-continued

<210> SEQ ID NO 43
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for succinimido-PEG20K residue, the succinimido-PEG20K residue being linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 43

```
Gly His Arg Pro Leu Asp Lys Lys Arg Glu Glu Ala Pro Ala Leu Arg
1               5                   10                  15

Pro Ala Pro Pro Pro Ile Ala Gly Gly Gly Tyr Arg Cys
            20                  25
```

<210> SEQ ID NO 44
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for succinimido-PEG10K residue, the succinimido-PEG10K residue being linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 44

```
Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Cys
            20                  25
```

<210> SEQ ID NO 45
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for succinimido-PEG20K residue, the succinimido-PEG20K residue being linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 45

```
Gly His Arg Pro Leu Asp Lys Lys Arg Glu Glu Ala Pro Ser Leu Arg
1               5                   10                  15
```

-continued

Pro Ala Pro Pro Pro Ile Ser Gly Gly Gly Tyr Arg Cys
20 25

<210> SEQ ID NO 46
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for succinimido-PEG20K residue, the succinimido-PEG20K residue being linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 46

Gly His Arg Pro Leu Asp Lys Lys Arg Glu Glu Ala Pro Ser Ile Arg
1 5 10 15

Pro Ala Pro Pro Pro Ile Ser Gly Gly Gly Tyr Arg Cys
20 25

<210> SEQ ID NO 47
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for CH2-CO-NH-PEG20K residue which is linked to the sulfur atom of the cysteine residue

<400> SEQUENCE: 47

Gly His Arg Pro Leu Asp Lys Lys Arg Glu Glu Ala Pro Ser Leu Arg
1 5 10 15

Pro Ala Pro Pro Pro Ile Ser Gly Gly Gly Tyr Arg Cys
20 25

<210> SEQ ID NO 48
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for CH2-CO-NH-PEG20K residue which is linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 48

Gly His Arg Pro Leu Asp Lys Lys Arg Glu Glu Ala Pro Ser Leu Arg
1 5 10 15

Pro Ala Pro Pro Pro Ile Ser Gly Gly Gly Tyr Arg Cys
20 25

-continued

```
<210> SEQ ID NO 49
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (25)..(25)
<223> OTHER INFORMATION: binding site for CH2-CO-NH-PEG20K residue which
      is linked to the sulfur atom of the cysteine residue
<220> FEATURE:
<221> NAME/KEY: MOD_RES
<222> LOCATION: (28)..(28)
<223> OTHER INFORMATION: AMIDATION

<400> SEQUENCE: 49

Gly His Arg Pro Leu Asp Lys Lys Arg Glu Glu Ala Pro Ser Leu Arg
1               5                   10                  15

Pro Ala Pro Pro Pro Ile Ser Gly Cys Gly Tyr Arg
            20                  25


<210> SEQ ID NO 50
<211> LENGTH: 28
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (25)..(25)
<223> OTHER INFORMATION: binding site for CH2-CO-NH-PEG20K residue which
      is linked to the sulfur atom of the cysteine residue
<220> FEATURE:
<221> NAME/KEY: MOD_RES
<222> LOCATION: (28)..(28)
<223> OTHER INFORMATION: AMIDATION

<400> SEQUENCE: 50

Gly His Arg Pro Leu Asp Lys Lys Arg Glu Glu Ala Pro Ser Leu Arg
1               5                   10                  15

Pro Ala Pro Pro Pro Ile Ser Gly Cys Gly Tyr Arg
            20                  25


<210> SEQ ID NO 51
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for CH2-CO-NH-PEG20K residue which
      is linked to the sulfur atom of the cysteine residue

<400> SEQUENCE: 51

Gly His Arg Pro Ile Asp Lys Lys Arg Glu Glu Ala Pro Ser Leu Arg
1               5                   10                  15

Pro Ala Pro Pro Pro Ile Ser Gly Gly Gly Tyr Arg Cys
            20                  25


<210> SEQ ID NO 52
<211> LENGTH: 29
<212> TYPE: PRT
<213> ORGANISM: Artificial Sequence
<220> FEATURE:
```

-continued

<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for CH2-CO-NH-PEG10K residue which
      is linked to the sulfur atom of the cysteine residue

<400> SEQUENCE: 52

Gly His Arg Pro Leu Asp Arg Lys Arg Glu Glu Ala Pro Ser Leu Arg
1               5                   10                  15

Pro Ala Pro Pro Pro Ile Ser Gly Gly Gly Tyr Arg Cys
            20                  25

<210> SEQ ID NO 53
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for CH2-CO-NH-PEG20K residue which
      is linked to the sulfur atom of the cysteine residue

<400> SEQUENCE: 53

Gly His Arg Pro Leu Asp Lys Lys Arg Glu Asp Ala Pro Ser Leu Arg
1               5                   10                  15

Pro Ala Pro Pro Pro Ile Ser Gly Gly Gly Tyr Arg Cys
            20                  25

<210> SEQ ID NO 54
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for CH2-CO-NH-PEG20K residue which
      is linked to the sulfur atom of the cysteine residue

<400> SEQUENCE: 54

Gly His Arg Pro Leu Asp Lys Lys Arg Glu Glu Ala Pro Ala Leu Arg
1               5                   10                  15

Pro Ala Pro Pro Pro Ile Ser Gly Gly Gly Tyr Arg Cys
            20                  25

<210> SEQ ID NO 55
<211> LENGTH: 29
<212> TYPE: PRT
<213> ORGANISM: Artificial Sequence
<220> FEATURE:
<223> OTHER INFORMATION: Synthesized peptide derivative of Bbeta (15-28)
      fibrin fragment
<220> FEATURE:
<221> NAME/KEY: BINDING
<222> LOCATION: (29)..(29)
<223> OTHER INFORMATION: binding site for CH2-CO-NH-PEG20K residue which
      is linked to the sulfur atom of the cysteine residue

<400> SEQUENCE: 55

Gly His Arg Pro Leu Asp Lys Lys Arg Glu Glu Ala Pro Ala Leu Arg
1               5                   10                  15

-continued

Pro Ala Pro Pro Pro Ile Ala Gly Gly Gly Tyr Arg Cys
            20                  25

<210> SEQ ID NO 56
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for CH2-CO-NH-PEG10K residue which is linked to the sulfur atom of the cysteine residue

<400> SEQUENCE: 56

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Cys
            20                  25

<210> SEQ ID NO 57
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for CH2-CO-NH-PEG20K residue which is linked to the sulfur atom of the cysteine residue

<400> SEQUENCE: 57

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Cys
            20                  25

<210> SEQ ID NO 58
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for CH2-CO-NH-PEG20K residue which is linked to the sulfur atom of the cysteine residue

<400> SEQUENCE: 58

Gly His Arg Pro Leu Asp Lys Lys Arg Glu Glu Ala Pro Ser Ile Arg
1               5                   10                  15

Pro Ala Pro Pro Pro Ile Ser Gly Gly Gly Tyr Arg Cys
            20                  25

<210> SEQ ID NO 59
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING -continued
<222> LOCATION: (29)..(29)
<223> OTHER INFORMATION: binding site for CH2-CO-NH-PEG20K residue which is linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 59

```
Gly His Arg Pro Ile Asp Lys Lys Arg Glu Glu Ala Pro Ser Leu Arg
1               5                   10                  15

Pro Ala Pro Pro Pro Ile Ser Gly Gly Gly Tyr Arg Cys
            20                  25
```

<210> SEQ ID NO 60
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for CH2-CO-NH-PEG10K residue which is linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 60

```
Gly His Arg Pro Leu Asp Arg Lys Arg Glu Glu Ala Pro Ser Leu Arg
1               5                   10                  15

Pro Ala Pro Pro Pro Ile Ser Gly Gly Gly Tyr Arg Cys
            20                  25
```

<210> SEQ ID NO 61
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for CH2-CO-NH-PEG20K residue which is linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 61

```
Gly His Arg Pro Leu Asp Lys Lys Arg Glu Asp Ala Pro Ser Leu Arg
1               5                   10                  15

Pro Ala Pro Pro Pro Ile Ser Gly Gly Gly Tyr Arg Cys
            20                  25
```

<210> SEQ ID NO 62
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)

-continued

<220> FEATURE:
<221> NAME/KEY: MOD_RES
<222> LOCATION: (29)..(29)
<223> OTHER INFORMATION: AMIDATION

<400> SEQUENCE: 62

Gly His Arg Pro Leu Asp Lys Lys Arg Glu Glu Ala Pro Ala Leu Arg
1 5 10 15

Pro Ala Pro Pro Pro Ile Ser Gly Gly Gly Tyr Arg Cys
20 25

<210> SEQ ID NO 63
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for CH2-CO-NH-PEG20K residue which is linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 63

Gly His Arg Pro Leu Asp Lys Lys Arg Glu Glu Ala Pro Ala Leu Arg
1 5 10 15

Pro Ala Pro Pro Pro Ile Ala Gly Gly Gly Tyr Arg Cys
20 25

<210> SEQ ID NO 64
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for CH2-CO-NH-PEG10K residue which is linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 64

Gly His Arg Pro Leu Asp Lys Lys Arg Glu Glu Ala Pro Ser Leu Arg
1 5 10 15

Pro Ala Pro Pro Pro Ile Ser Gly Gly Gly Tyr Arg Cys
20 25

<210> SEQ ID NO 65
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for CH2-CO-NH-PEG20K residue which is linked to the sulfur atom of the cysteine residue
<220> FEATURE:

-continued

<221> NAME/KEY: MOD_RES
<222> LOCATION: (29)..(29)
<223> OTHER INFORMATION: AMIDATION

<400> SEQUENCE: 65

Gly His Arg Pro Leu Asp Lys Lys Arg Glu Glu Ala Pro Ser Leu Arg
1 5 10 15

Pro Ala Pro Pro Pro Ile Ser Gly Gly Gly Tyr Arg Cys
20 25

<210> SEQ ID NO 66
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: BINDING
<222> LOCATION: (29)..(29)
<223> OTHER INFORMATION: binding site for CH2-CO-NH-PEG20K residue which is linked to the sulfur atom of the cysteine residue
<220> FEATURE:
<221> NAME/KEY: MOD_RES
<222> LOCATION: (29)..(29)
<223> OTHER INFORMATION: AMIDATION

<400> SEQUENCE: 66

Gly His Arg Pro Leu Asp Lys Lys Arg Glu Glu Ala Pro Ser Ile Arg
1 5 10 15

Pro Ala Pro Pro Pro Ile Ser Gly Gly Gly Tyr Arg Cys
20 25

<210> SEQ ID NO 67
<211> LENGTH: 29
<212> TYPE: PRT
<213> ORGANISM: Artificial Sequence
<220> FEATURE:
<223> OTHER INFORMATION: Synthesized peptide derivative of Bbeta (15-28) fibrin fragment
<220> FEATURE:
<221> NAME/KEY: MISC_FEATURE
<222> LOCATION: (29)..(29)
<223> OTHER INFORMATION: Xaa denotes C or is absent
<220> FEATURE:
<221> NAME/KEY: MISC_FEATURE
<222> LOCATION: (29)..(29)
<223> OTHER INFORMATION: amino acid modified with (NR2R3)-(S-succinimido)-PEG5-60K, R2 and R3 being identical or different and denoting hydrogen or (C1-C10)-alkyl and the succinimido residue being linked to a sulfur atom of the cysteine residue via C-atom 3

<400> SEQUENCE: 67

Gly His Arg Pro Leu Asp Lys Lys Arg Glu Glu Ala Pro Ser Leu Arg
1 5 10 15

Pro Ala Pro Pro Pro Ile Ser Gly Gly Gly Tyr Arg Xaa
20 25

The invention claimed is:

1. A peptide of Formula (II), $H_2N$-GHRPLDKKREEAPSLRPAPPPISGGGYR-$X_{17}$ (II) (SEQ ID NO: 67), wherein: $X_{17}$ denotes a residue $C(NR_2R_3)$-(S-succinimido)-($PEG_{5-60K}$), the succinimido residue being linked to the sulfur atom of the cysteine residue via C-atom 3, and $R_2$ and $R_3$ being identical or different and being hydrogen or ($C_1$-$C_{10}$)-alkyl, as well as a physiologically acceptable salt thereof.

2. A peptide of Formula (III), $H_2N$-GHRPLDKKREEAPSLRPAPPPIS-$X_{19}$-$X_{20}$-$X_{21}$-YR-$X_{17}$ (III) (SEQ ID NO: 10), wherein two of the residues $X_{19}$, $X_{20}$ and $X_{21}$ each are a glycine residue and the remaining one is a residue C-(S-succinimido)-($PEG_{5-40K}$), the succinimido residue being linked to the sulfur atom of the cysteine residue via C-atom 3, and wherein $X_{17}$ denotes $NR_2R_3$, $R_2$ and $R_3$ being identical or different and being hydrogen or ($C_1$-$C_{10}$)-alkyl, as well as a physiologically acceptable salt thereof.

3. A peptide of Formula (III), $H_2N$-GHRPLDKKREEAPSLRPAPPPIS-$X_{19}$-$X_{20}$-$X_{21}$-YR-$X_{17}$ (III) (SEQ ID NO: 11), wherein two of the residues $X_{19}$, $X_{20}$ and $X_{21}$ each are a glycine residue and the remaining one is a residue K-($PEG_{5-40K}$), the PEG-residue being linked via the nitrogen atom in the side chain of the lysine residue, and wherein $X_{17}$ denotes $NR_2R_3$, $R_2$ and $R_3$ being identical or different and being hydrogen or ($C_1$-$C_{10}$)-alkyl, as well as a physiologically acceptable salt thereof.

4. A pharmaceutical drug composition, containing the peptide according to any of claims 1 to 3.

* * * * *